United States Patent
Takeshima

(10) Patent No.: US 10,987,021 B2
(45) Date of Patent: Apr. 27, 2021

(54) MEDICAL IMAGE DIAGNOSTIC APPARATUS, MEDICAL SIGNAL RESTORATION METHOD, AND MODEL TRAINING METHOD

(71) Applicant: CANON MEDICAL SYSTEMS CORPORATION, Otawara (JP)

(72) Inventor: Hidenori Takeshima, Kawasaki (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 54 days.

(21) Appl. No.: 16/352,892

(22) Filed: Mar. 14, 2019

(65) Prior Publication Data

US 2019/0282120 A1    Sep. 19, 2019

(30) Foreign Application Priority Data

Mar. 14, 2018   (JP) .............................. JP2018-046845

(51) Int. Cl.
*A61B 5/055*    (2006.01)
*A61B 6/03*    (2006.01)
(Continued)

(52) U.S. Cl.
CPC .............. *A61B 5/055* (2013.01); *A61B 6/035* (2013.01); *G01R 33/5611* (2013.01);
(Continued)

(58) Field of Classification Search
None
See application file for complete search history.

(56) References Cited

U.S. PATENT DOCUMENTS 7,054,474 B1 *  5/2006  Krieger ................... G06T 5/002
                                                                348/241
2009/0278539 A1    11/2009  Beatty
(Continued)

FOREIGN PATENT DOCUMENTS

EP         3719750 A1 *  7/2020
JP         2009-268901    11/2009

OTHER PUBLICATIONS

Liu, Risheng, Shiqi Li, Jinyuan Liu, Long Ma, Xin Fan, and Zhongxuan Luo. "Learning Hadamard-Product-Propagation for Image Dehazing and Beyond." IEEE Transactions on Circuits and Systems for Video Technology (2020). (Year: 2020).*

(Continued)

*Primary Examiner* — Michelle M Entezari
(74) *Attorney, Agent, or Firm* — Oblon, McClelland, Maier & Neustadt, L.L.P.

(57) ABSTRACT

According to one embodiment, a medical image diagnostic apparatus includes processing circuitry. The processing circuitry configured to generate initial restored signal data by applying a first restoration function to input signal data corresponding to medical signal data concerning an object, generate first element-wise product signal data by calculating an element-wise product of the initial restored signal data and reliability data representing a degree of degradation included in the input signal data, and generate restored signal data by applying a second restoration function to at least one of the input signal data and the initial restored signal data and the first element-wise product signal data.

15 Claims, 27 Drawing Sheets

(51) Int. Cl.
*A61B 6/00* (2006.01)
*A61B 5/00* (2006.01)
*G01R 33/561* (2006.01)
*G06N 3/08* (2006.01)

(52) U.S. Cl.
CPC .......... *G01R 33/5619* (2013.01); *G06N 3/08* (2013.01); *A61B 5/0033* (2013.01); *A61B 6/5205* (2013.01); *G06T 2207/10081* (2013.01); *G06T 2207/20056* (2013.01); *G06T 2207/20081* (2013.01); *G06T 2207/30004* (2013.01)

(56) References Cited

U.S. PATENT DOCUMENTS

| | | | | |
|---|---|---|---|---|
| 2010/0215282 A1* | 8/2010 | Van Beek | ................ | G06T 5/50 382/255 |
| 2012/0148129 A1* | 6/2012 | Chang | .............. | G01R 33/56545 382/131 |
| 2013/0129233 A1* | 5/2013 | Schiller | ................ | G06T 11/60 382/228 |
| 2014/0160323 A1* | 6/2014 | Rao | ........................ | G06T 5/30 348/242 |
| 2014/0200820 A1* | 7/2014 | El Yadari | ............... | G01V 1/364 702/17 |
| 2015/0262590 A1* | 9/2015 | Joder | ................ | G10L 21/0232 704/201 |
| 2017/0103522 A1* | 4/2017 | Omi | ........................ | G06T 7/73 |
| 2017/0135659 A1* | 5/2017 | Wang | ................ | A61B 6/5258 |
| 2019/0139199 A1* | 5/2019 | Wang | ........................ | G06T 5/30 |

OTHER PUBLICATIONS

Guo, Yina, Jianguo Chen, Xiaowen Ren, Anhong Wang, and Wenwu Wang. "Joint Raindrop and Haze Removal From a Single Image." IEEE Transactions on Image Processing 29 (2020): 9508-9519. (Year: 2020).*

Shen, Ziyi, Huazhu Fu, Jianbing Shen, and Ling Shao. "Modeling and Enhancing Low-Quality Retinal Fundus Images." IEEE Transactions on Medical Imaging (2020). (Year: 2020).*

J. Xie, et al., "Image Denoising and Inpainting with Deep Neural Networks", NeUral Information Processing Systems 25 (NIPS 2012), 2012, 9 pages.

J. Schlemper, et al., A Deep Cascade of Convolutional Neural Networks for MR Image Reconstruction:, arXiv:1703.00555v1[cs.CV], Mar. 1, 2017, 12 pages.

* cited by examiner

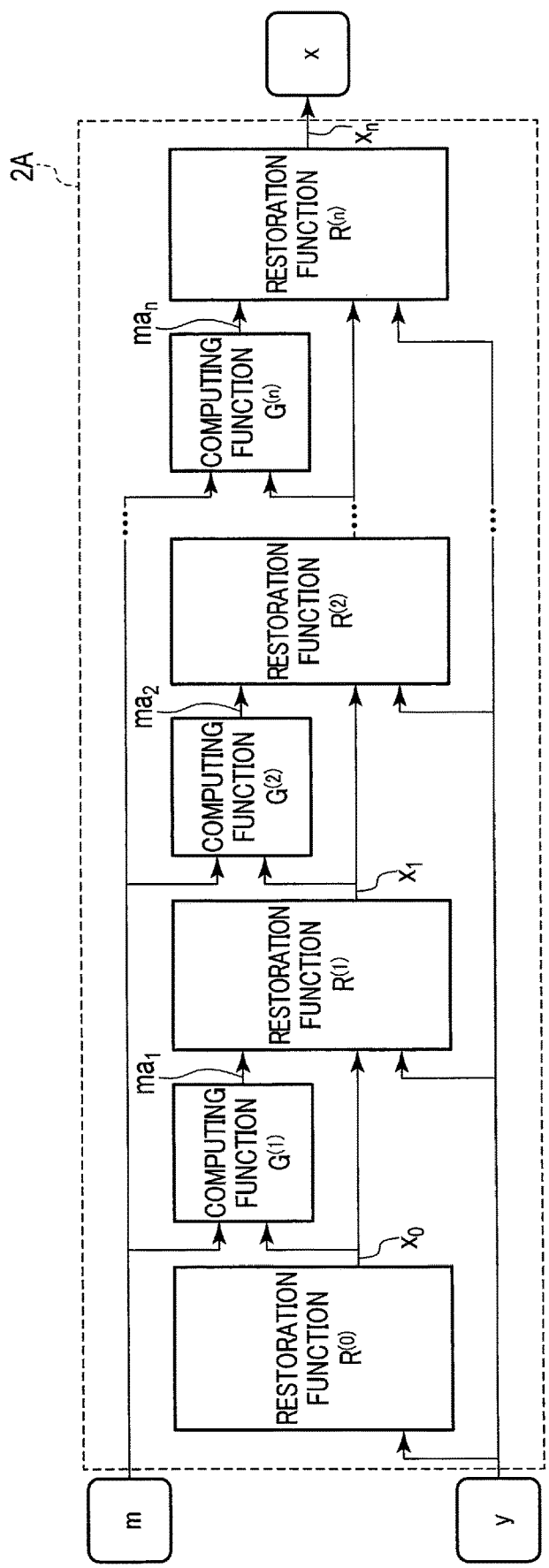
F I G. 4

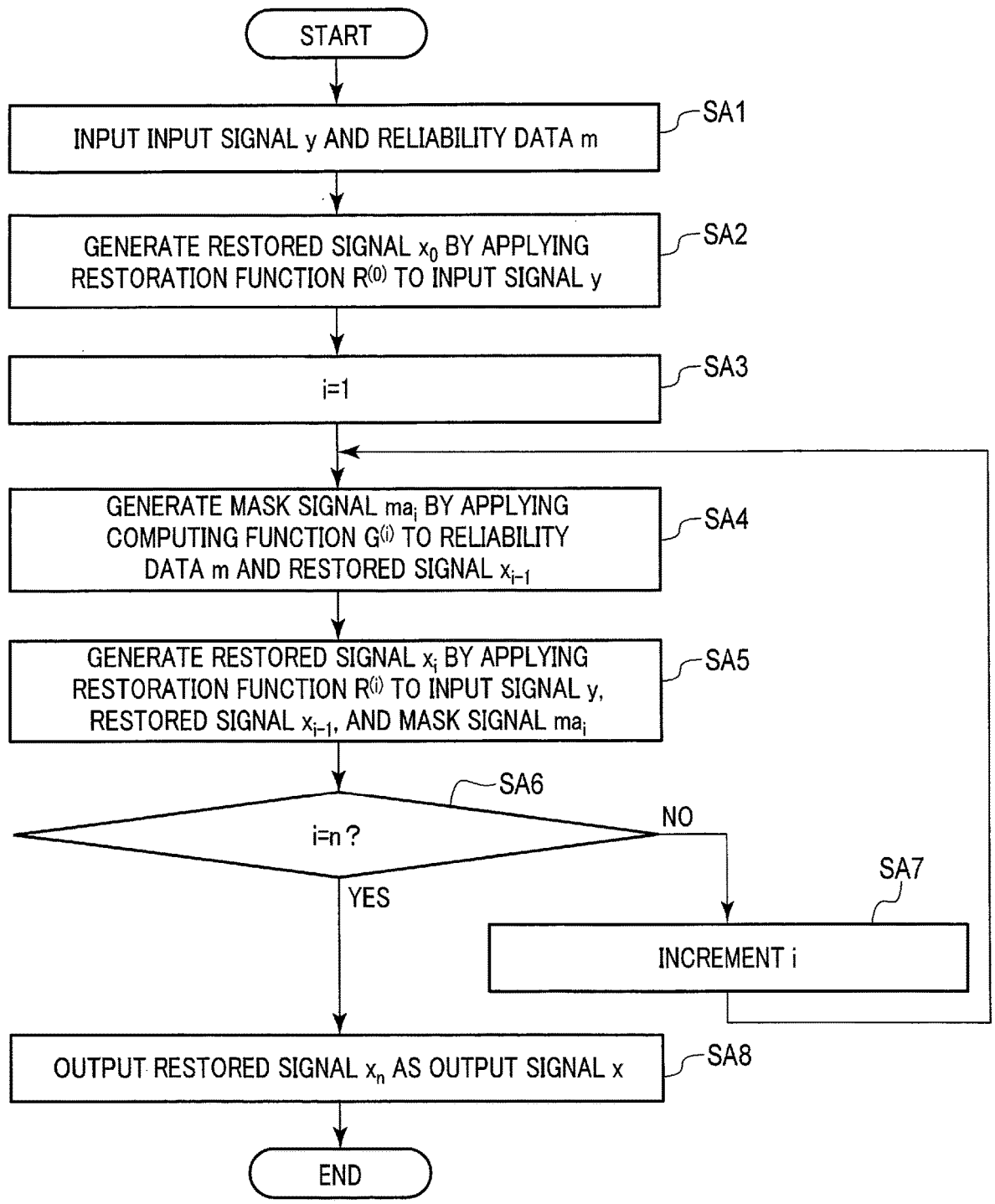
F I G. 5

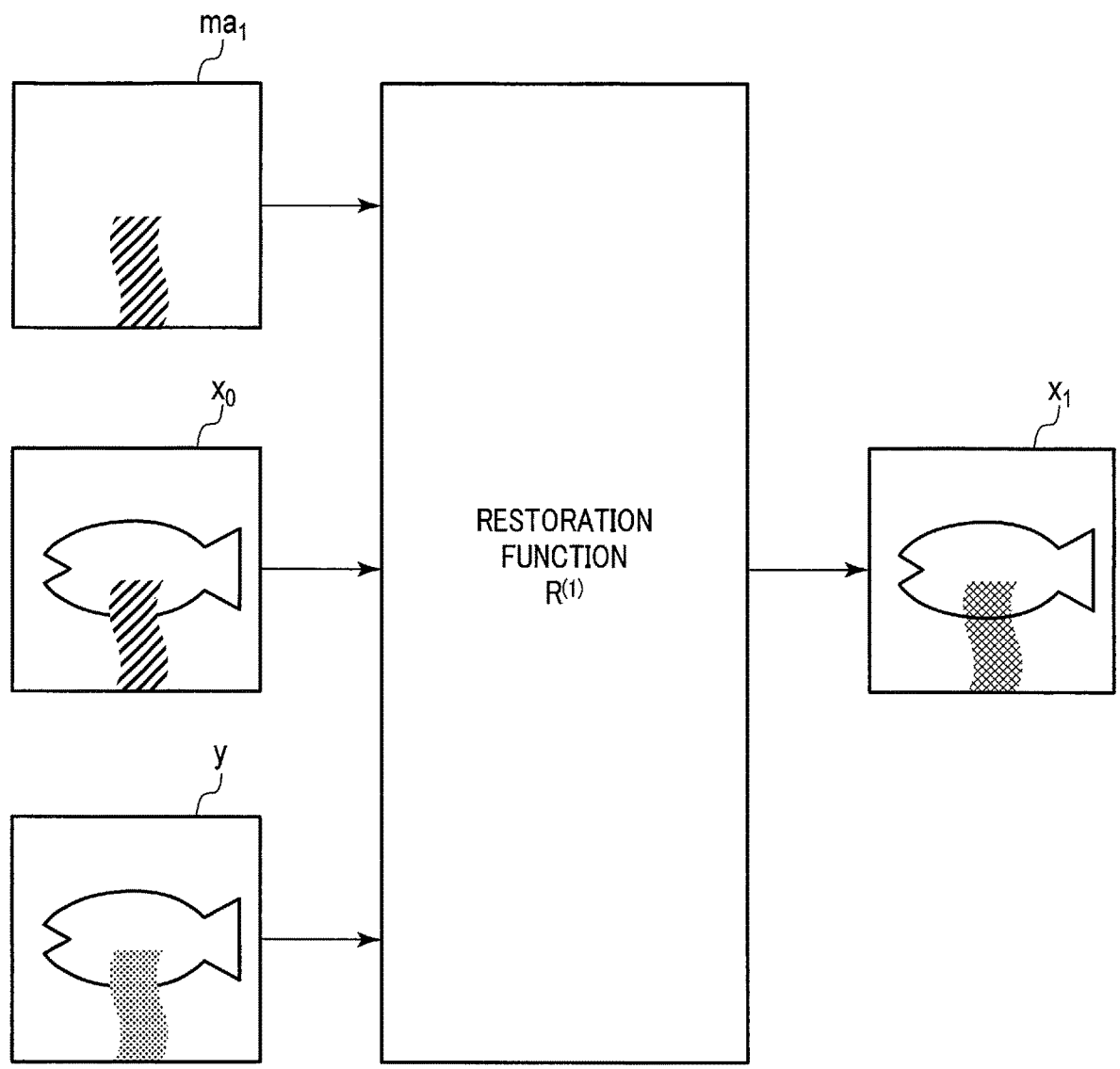
F I G. 8

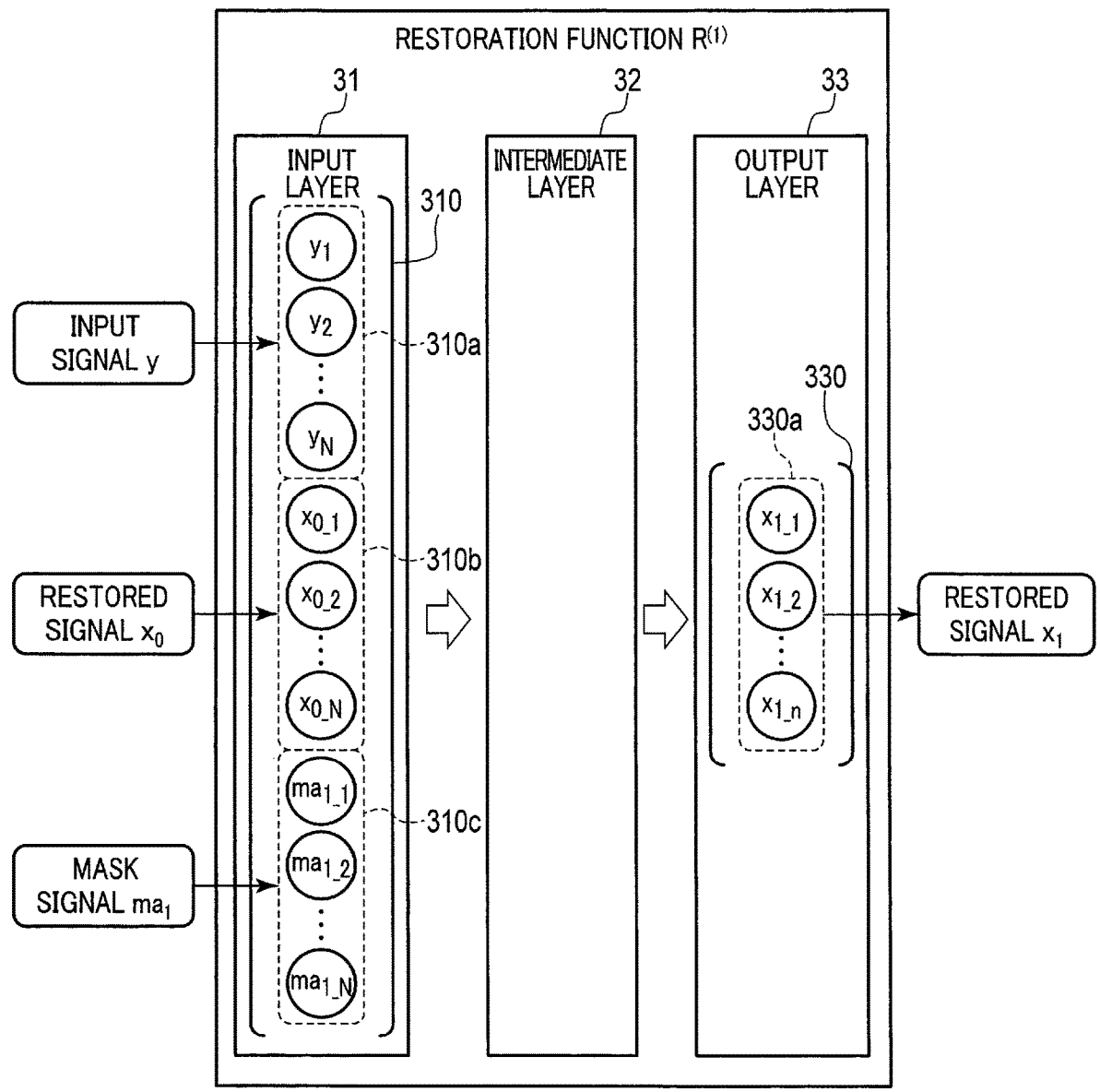
F I G. 9

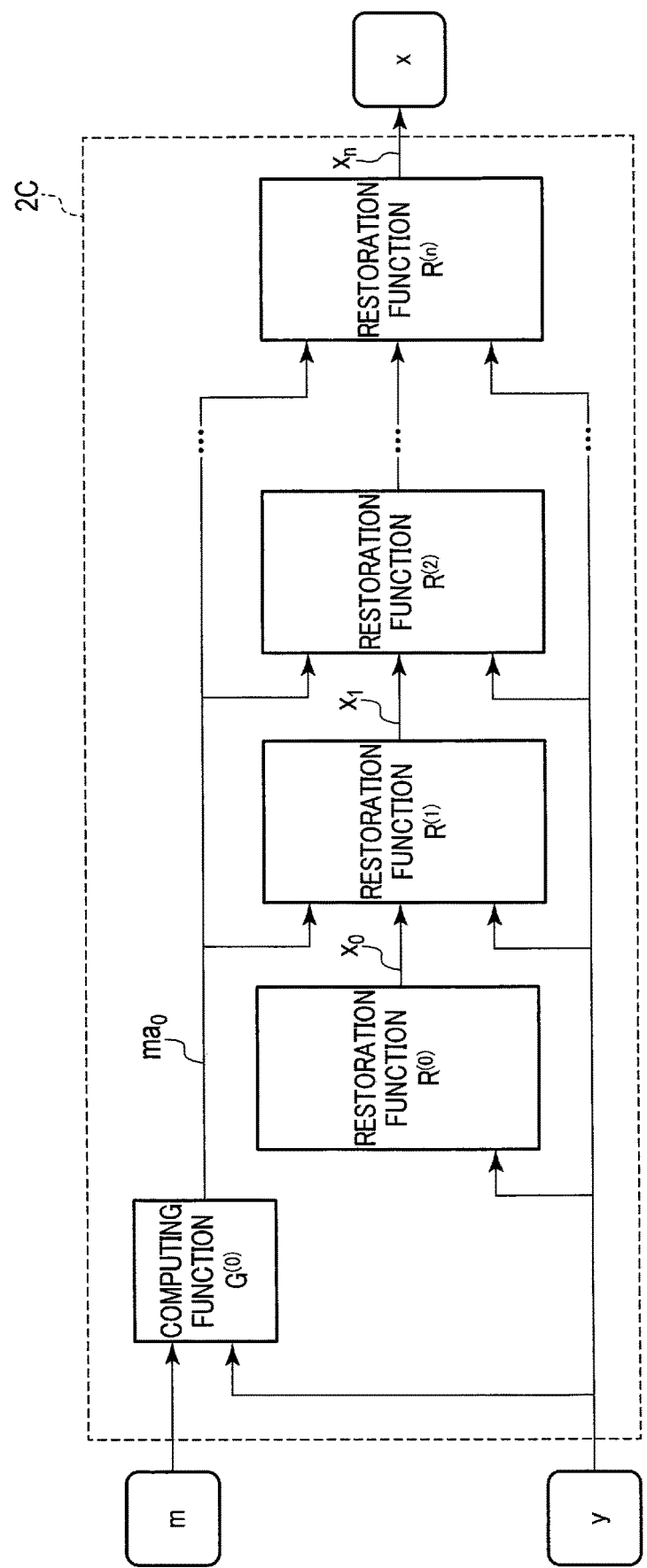
F I G. 13

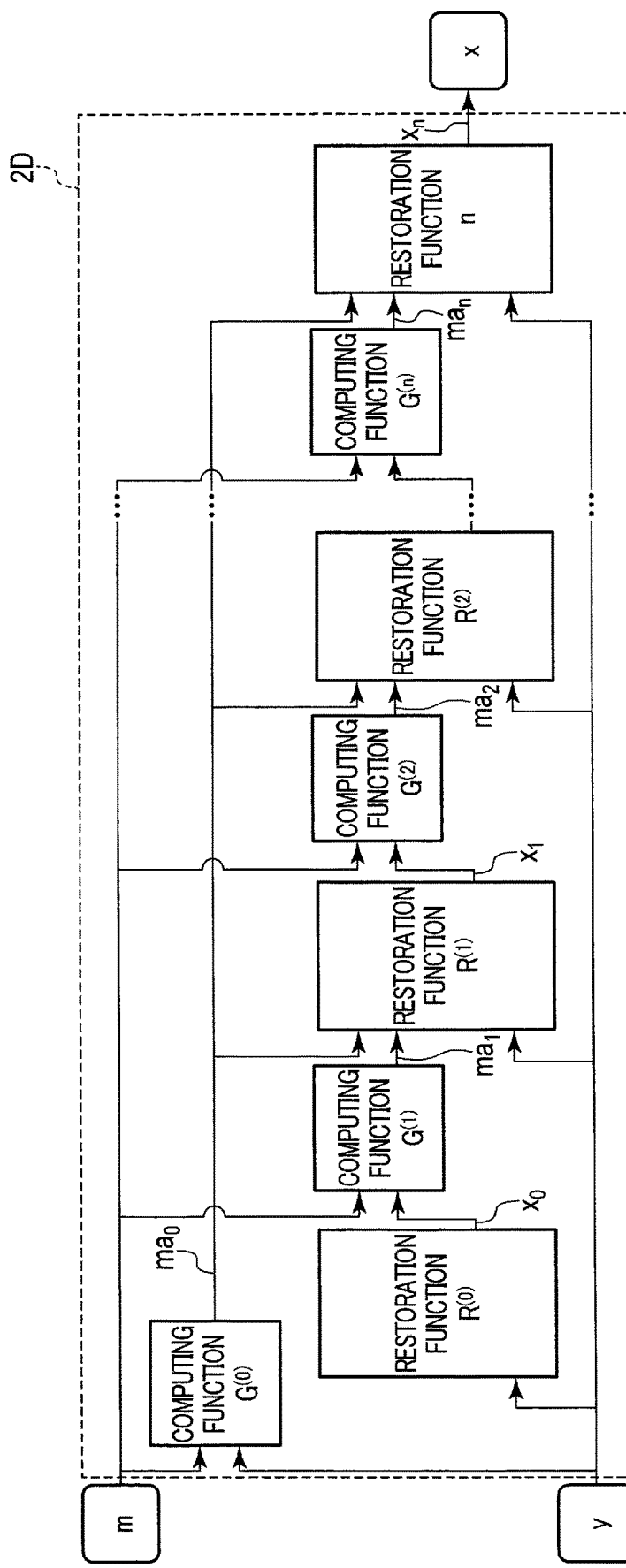
F I G. 15

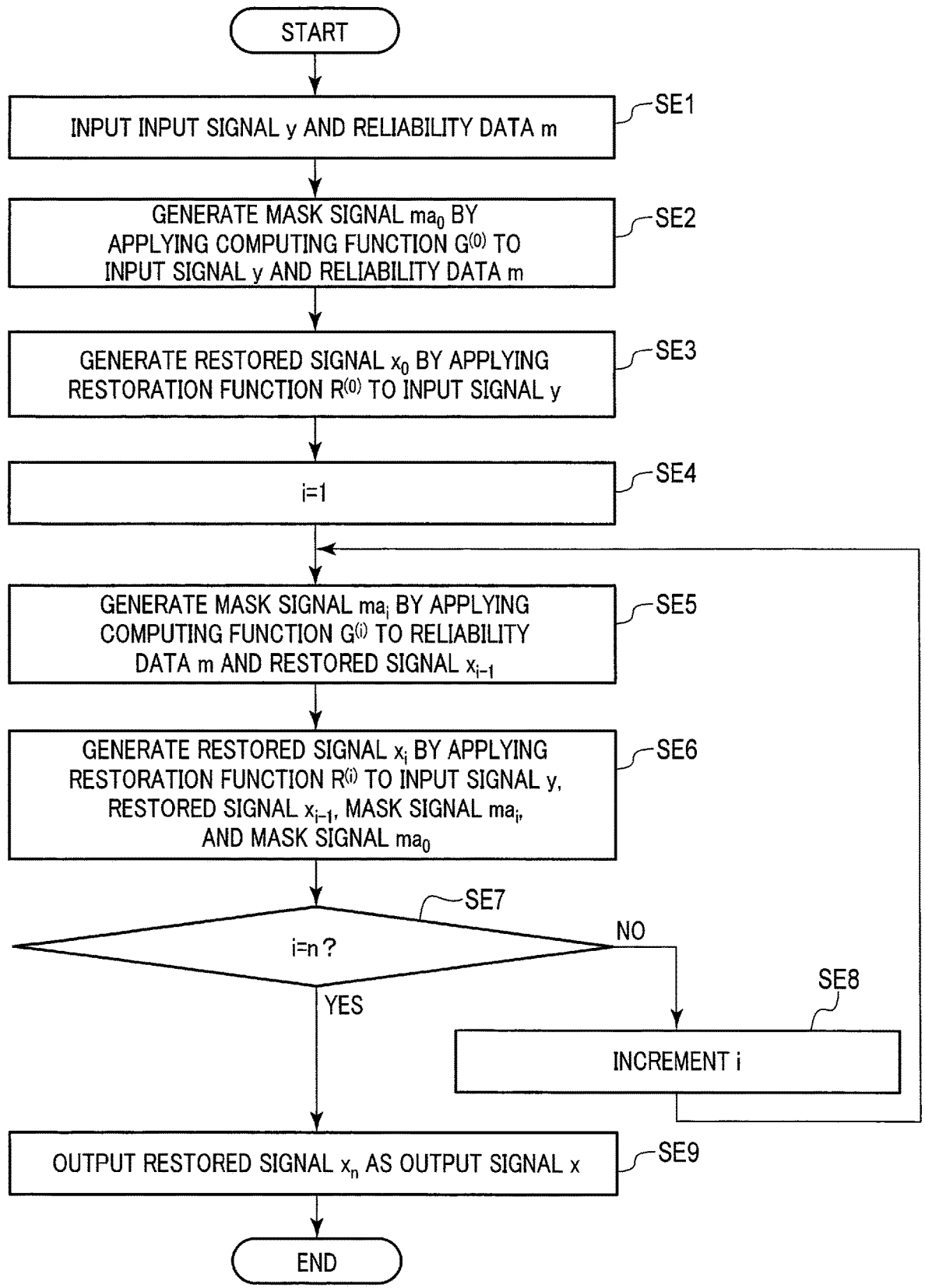
F I G. 18

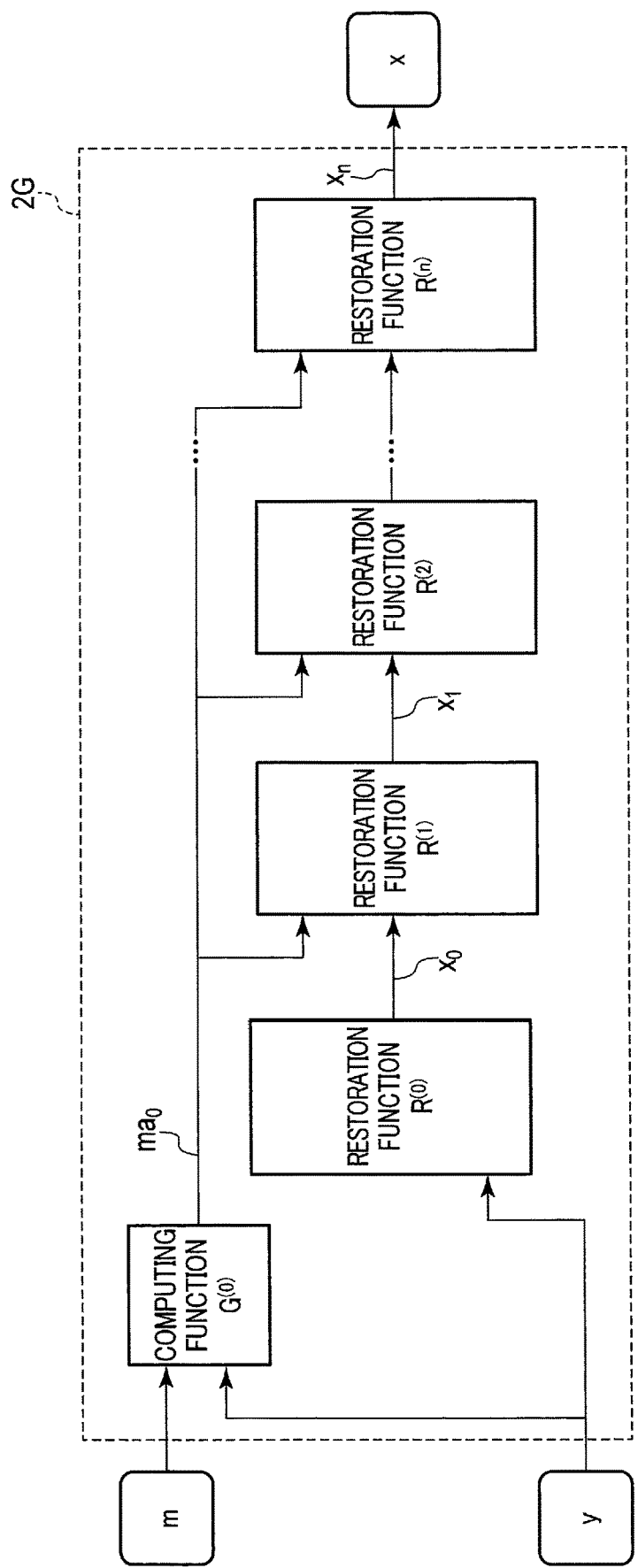
F I G. 20

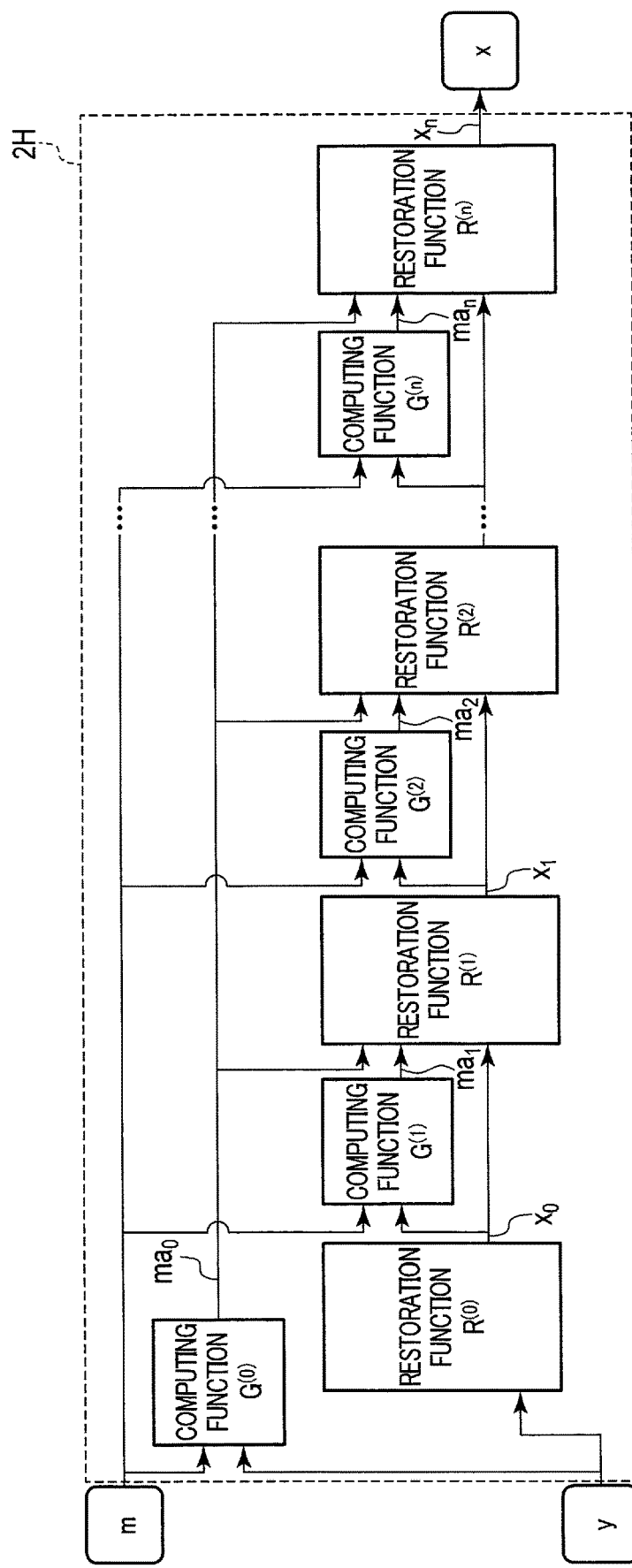
F I G. 21

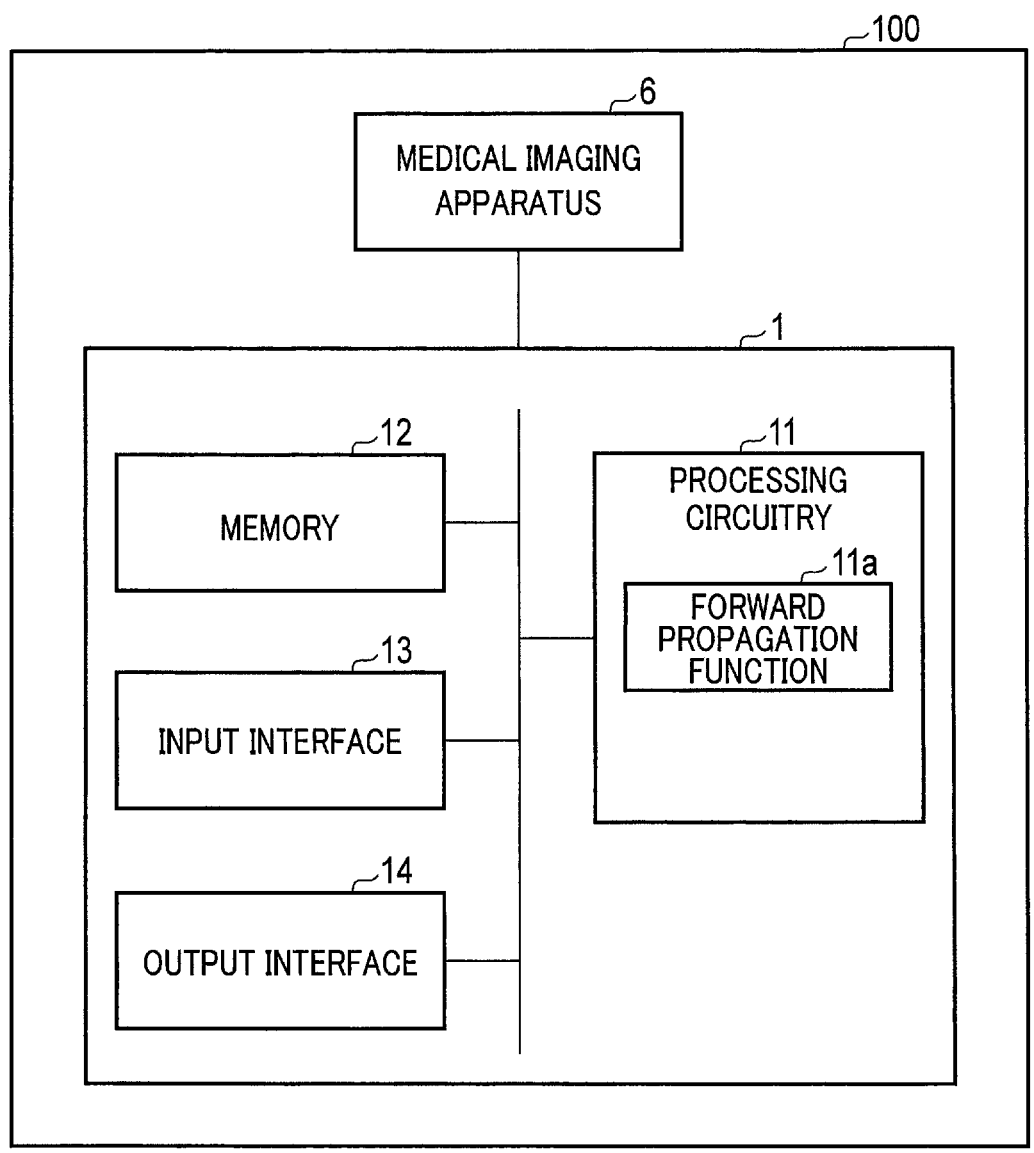
F I G. 24

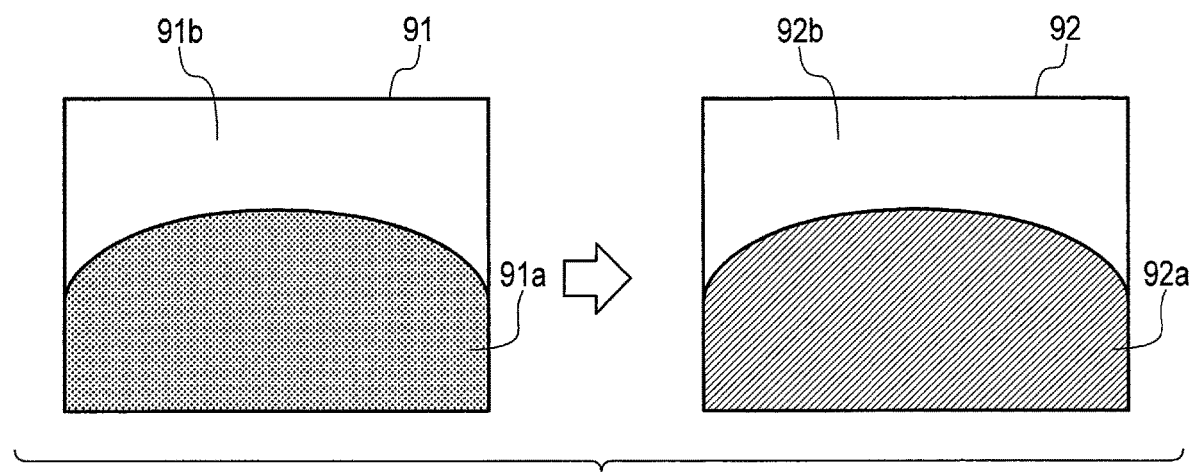
F I G. 31

US 10,987,021 B2

MEDICAL IMAGE DIAGNOSTIC APPARATUS, MEDICAL SIGNAL RESTORATION METHOD, AND MODEL TRAINING METHOD

CROSS-REFERENCE TO RELATED APPLICATIONS

This application is based upon and claims the benefit of priority from Japanese Patent Application No. 2018-046845, filed Mar. 14, 2018, the entire contents of which are incorporated herein by reference.

FIELD

Embodiments described herein relate generally to a medical image diagnostic apparatus, a medical signal restoration method, and a model training method.

BACKGROUND

There is available a technique using a DNN (Deep Neural Network) trained from a large amount of training data to restore an original signal from data lacking in part of a signal. Assume that a portion of a given image is lost, and the lost portion is unknown. There is available a technique of restoring the original image by compensating for the lost portion. In addition, there is available a technique of generating k-space data by restoring a lost portion of undersampled k-space data by applying DNN to the data and then obtaining a restored image based on the k-space data after restoration.

BRIEF DESCRIPTION OF THE DRAWINGS

FIG. 4 is a block diagram showing an example of the arrangement of a trained model according to the first embodiment;

FIG. 5 is a flowchart showing a procedure for signal restoration processing in the arrangement of the trained model in FIG. 4;

FIG. 8 is an explanatory diagram for a restoration function $R^{(1)}$ in FIG. 4;

FIG. 9 is a block diagram showing a specific example of the arrangement of the restoration function $R^{(1)}$ in FIG. 4;

FIG. 13 is a block diagram showing another example of the arrangement of the trained model according to the first embodiment;

FIG. 15 is a block diagram showing another example of the arrangement of the trained model according to the first embodiment;

FIG. 18 is a flowchart showing a procedure for signal restoration processing in the arrangement of the trained model in FIG. 17;

FIG. 20 is a block diagram showing another example of the arrangement of the trained model according to the first embodiment;

FIG. 21 is a block diagram showing another example of the arrangement of the trained model according to the first embodiment;

FIG. 24 is a block diagram showing an example of the arrangement of a medical image diagnostic apparatus according to the second embodiment;

FIG. 31 is a view showing an example of distance image data and reliability data according to the third embodiment.

DETAILED DESCRIPTION

In general, according to one embodiment, a medical image diagnostic apparatus includes processing circuitry. The processing circuitry configured to generate initial restored signal data by applying a first restoration function to input signal data corresponding to medical signal data concerning an object, generate first element-wise product signal data by calculating an element-wise product of the initial restored signal data and reliability data representing a degree of degradation included in the input signal data, and generate restored signal data by applying a second restoration function to at least one of the input signal data and the initial restored signal data and the first element-wise product signal data.

First Embodiment

Figure 1:
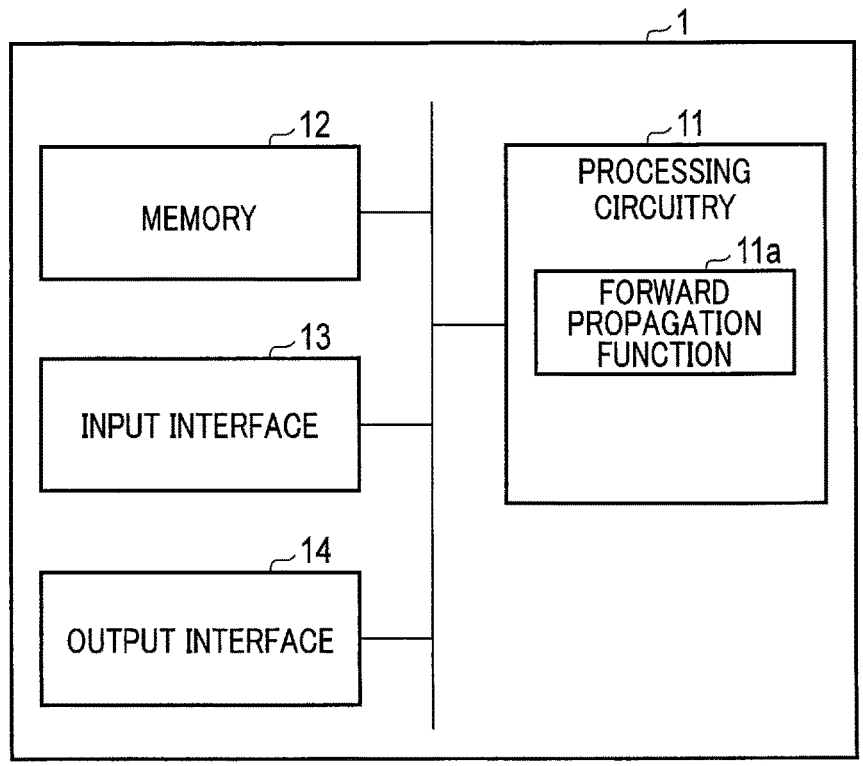
FIG. 1 is a block diagram showing an example of the arrangement of a signal restoration apparatus according to the first embodiment.

FIG. 1 is a block diagram showing an example of the arrangement of a signal restoration apparatus according to the first embodiment. A signal restoration apparatus 1 in FIG. 1 is an apparatus including a feed forward (forward propagation) function in a DNN. The signal restoration apparatus 1 is implemented by an integrated circuit such as an ASIC (Application Specific Integrated Circuit) or FPGA (Field-Programmable Gate Array). Assume that in the following description, the signal restoration apparatus 1 is an ASIC.

As shown in FIG. 1, the signal restoration apparatus 1 according to this embodiment includes processing circuitry 11, a memory 12, an input interface 13, and an output interface 14. The processing circuitry 11, the memory 12, the input interface 13, and the output interface 14 are connected to each other via a bus.

The processing circuitry 11 is a combination of circuit elements or logic circuits designed to execute a forward propagation function 11a. The forward propagation function 11a is, for example, a function of estimating (generating) an output with respect to inputs by using a trained machine learning model (to be referred to as the trained model hereinafter) in a feed forward network in a DNN.

Figure 2:
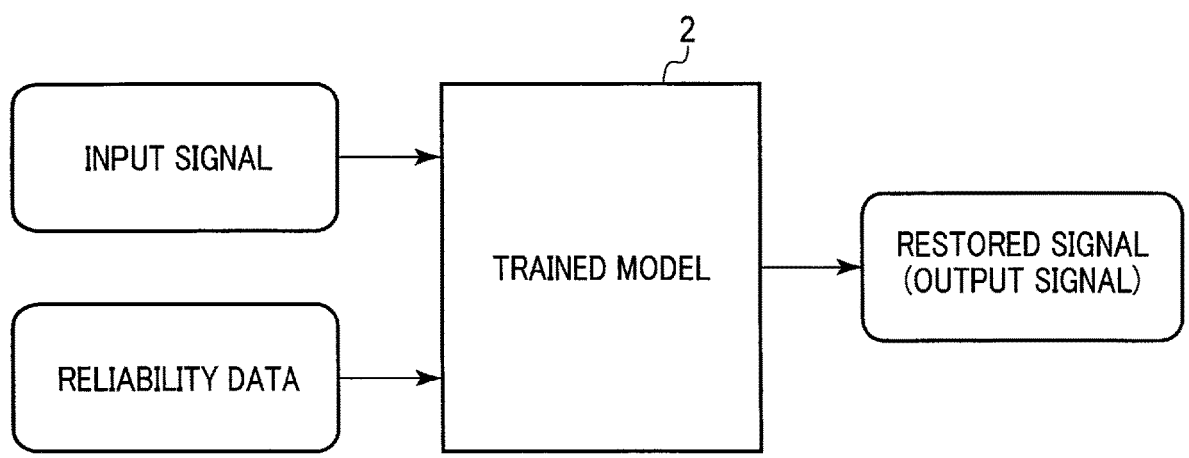
FIG. 2 is a block diagram showing an example of a combination of inputs and an output of a trained model according to the first embodiment.

FIG. 2 is a block diagram showing an example of a combination of inputs and an output in a trained model according to the first embodiment. A trained model 2 in FIG. 2 is used in the forward propagation function 11a of the processing circuitry 11. The processing circuitry 11 generates an output signal (restored signal) by applying the trained model 2 to an input signal input via the input interface 13 and reliability data concerning the input signal. The processing circuitry 11 then outputs the generated restored signal via the output interface 14. Note that an input signal and a restored signal may be called input signal data and restored signal data, respectively.

Reliability data is data representing the reliability of an input signal. Reliability represents, for example, the degree of degradation included in an input signal. More specifically, reliability data has information indicating, for example, a lost portion in an input signal and a portion other than the lost portion. A lost portion is, for example, a portion having a value different from the value (for example, the pixel value) of a portion lacking in data or a target to be restored. Reliability data can be expressed as mask data representing a lost portion by "0" and a portion other than the lost portion by "1". That is, an input signal having a lost portion can be regarded as a signal obtained by applying mask data to a restored signal. Accordingly, an input signal is sometimes expressed as a "degraded signal".

Reliability data may also have, for example, information indicating the likelihood of an input signal. In this case, reliability data is expressed as non-binary mask data representing the likelihood of a signal by using a numerical value (for example, a floating-point value) between "0" and "1". For example, when an input signal is expressed as data (input image) corresponding to an image, reliability data has numerical information at a position corresponding to a pixel position of the input image (for example, the position of a vector element).

As reliability data, a lost portion is expressed as "0", and a portion other than the lost portion is expressed as "1", while the likelihood of an input signal is expressed by a numerical value between "0" and "1". However, this is not exhaustive. Reliability data may be expressed by any numerical value as long as numerical values respectively corresponding to a "lost portion", a "portion other than the lost portion", and the "likelihood of an input signal" are defined.

When executing the forward propagation function 11a, the processing circuitry 11 accepts inputs of an input signal and reliability data. The processing circuitry 11 then applies the trained model 2 to the input signal and the reliability data to generate a restored signal corresponding to the input signal. The restored signal is a signal obtained by restoring the signal lost portion included in the input signal. That is, the trained model 2 is a DNN that has trained parameters so as to input an input signal including a signal loss and reliability data specifying the signal loss and output a signal that does not include the signal loss. Parameters are, for example, a combination of a weighted matrix and biases in a feed forward network. Note that the trained model 2 may be implemented by a plurality of DNNs.

The memory 12 is a circuit element that stores arbitrary information, such as a ROM (Read Only Memory) and a RAM (Random Access Memory). For example, the memory 12 stores the calculation result obtained at the time of the execution of the forward propagation function 11a.

The input interface 13 is an interface for inputting to the processing circuitry 11. The input interface 13 inputs, for example, an input signal and reliability data to the processing circuitry 11. For example, the computer mounted in the signal restoration apparatus 1 selects the input signal and the reliability data.

The output interface 14 is an interface for outputting from the processing circuitry 11. The output interface 14 outputs, for example, the restored signal output from the processing circuitry 11 to a computer, network, storage device, or the like.

Figure 3:
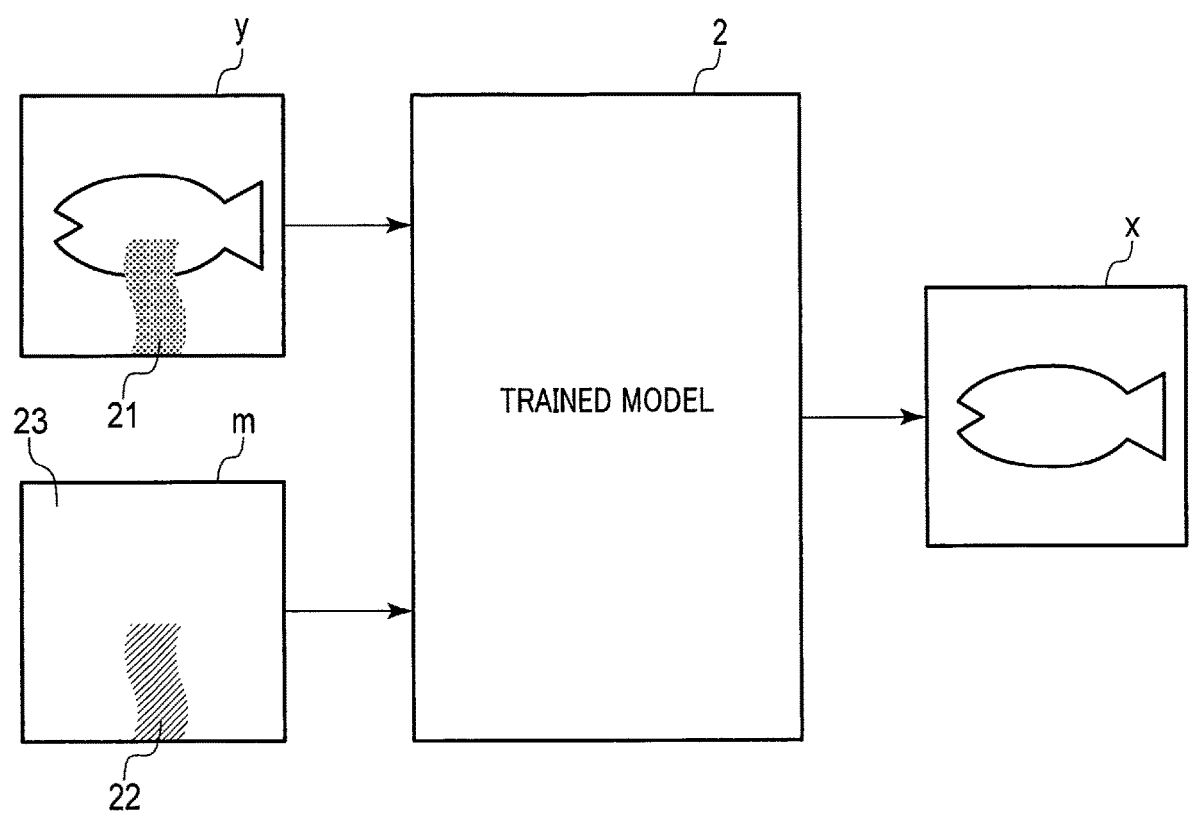
FIG. 3 is a block diagram showing a specific example of a combination of inputs and an output of a trained model according to the first embodiment.

FIG. 3 is a block diagram showing a specific example of a combination of inputs and an output of a trained model according to the first embodiment. As shown in FIG. 3, the trained model 2 accepts an input of an input signal y and an input of reliability data m.

The input signal y corresponds to, for example, medical image data or distance image data. For the sake of descriptive convenience, the following description will be made assuming that the input signal y is regarded as image data. However, the input signal is not limited to image data.

The input signal y includes, for example, a lost portion 21. The lost portion 21 is, for example, a portion that is masked and has a pixel value different from a proper pixel value or a shielded portion of a desired image.

The reliability data m is data concerning the reliability of each pixel value of the input signal y. The reliability data m includes lost data 22 and acquired data 23. The lost data 22 corresponds to the lost portion 21 of the input signal y, and is expressed by, for example, the numerical value "0". The acquired data 23 corresponds to a portion other than the lost portion 21, and is expressed by, for example, the numerical value "1".

The trained model 2 is applied to the input signal y and the reliability data m to generate a restored signal x corresponding to the input signal y. The restored signal x corresponds to the input signal y obtained by restoring the lost portion 21 included in the input signal y.

FIG. 4 is a block diagram showing an example of the arrangement of a trained model according to the first embodiment. As shown in FIG. 4, a trained model 2A is constituted by a process of applying a restoration function $R^{(0)}$ to arbitrary data and a process of applying a combination of a computing function $G^{(i)}$ and a restoration function $R^{(i)}$ to the arbitrary data n times (i=1 to n (n is an integer equal to or more than 1)). Note that the "DNN that has trained parameters" is equivalent to a DNN with parameters of the respective functions being optimized. In addition, the restoration function $R^{(0)}$ may be called the first restoration function, and the restoration function $R^{(i)}$ may be called the second restoration function.

The restoration function $R^{(0)}$ is formed from, for example, a DNN. The restoration function $R^{(0)}$ performs computation to generate a restored signal $x_0$ from the input signal y. The restored signal $x_0$ is generated by, for example, applying the DNN to the input signal y. The processing circuitry 11 generates the restored signal $x_0$ by applying the restoration function $R^{(0)}$ to the input signal y. Note that the restored signal $x_0$ may be called an initial restored signal or initial restored signal data.

The restoration function $R^{(0)}$ may not be formed from a DNN. If the restoration function $R^{(0)}$ is not formed from a DNN, the restored signal $x_0$ is generated by, for example, estimating a lost portion included in the input signal y and replacing the lost portion with a neighborhood signal value. In addition, the restored signal $x_0$ may be generated by applying an arbitrary filter to the input signal y.

The computing function $G^{(i)}$ performs computation to generate a mask signal $ma_i$ (also called a first element-wise product signal) by performing element-wise multiplication (also called Hadamard multiplication) of a restored signal $x_{i-1}$ and the reliability data m. The mask signal $ma_i$ is obtained by, for example, extracting a masked portion (or a lost portion) in the restored signal $x_{i-1}$ based on the reliability data m. The processing circuitry 11 generates the mask signal $ma_i$ by applying the computing function $G^{(i)}$ to the reliability data m and the restored signal $x_{i-1}$. Note that a mask signal and a first element-wise product signal may be called mask signal data and first element-wise product signal data, respectively.

Two data subjected to element-wise multiplication (calculation of an element-wise product) preferably have the same number of elements. However, two data may have different numbers of elements. When two data have different numbers of elements, element-wise multiplication may be performed after processing like matching the number of elements of one data with the number of elements of the other data.

The restoration function $R^{(i)}$ is formed from, for example, a DNN. The restoration function $R^{(i)}$ performs computation to generate a restored signal $x_i$ from the input signal y, the restored signal $x_{i-1}$, and the mask signal $ma_i$. The restored signal $x_i$ is generated by, for example, applying the DNN to the input signal y, the restored signal $x_{i-1}$, and the mask signal $ma_i$. The processing circuitry 11 generates the restored signal $x_i$ by applying the restoration function $R^{(i)}$ to the input signal y, the restored signal $x_{i-1}$ output from a preceding restoration function $R^{(i-1)}$, and the mask signal $ma_i$. Note that a restored signal $x_n$ generated by a restoration function $R^{(n)}$ corresponds to the restored signal x.

The DNN used in the restoration function $R^{(0)}$ and the restoration function $R^{(i)}$ can be represented by a composite function including a combination of many functions. The many functions use, for example, a linear function, convolution, a ReLU (Rectified Linear Unit), each of which is also called a layer. A DNN including convolution is called a CNN in particular. CNNs may be used for the restoration function $R^{(0)}$ and the restoration function $R^{(i)}$. Note that a DNN may be expressed as a parameterized composite function.

The respective functions of the restoration function $R^{(i)}$ differ from each other. However, these functions need not always differ from each other. These functions of the restoration function $R^{(i)}$ may be the same under the condition of including, for example, a recurrent network function (for example, LSTM (Long Short Term Memory)). Note that the restoration function $R^{(0)}$ may be included in the above functions in the same manner.

FIG. 5 is a flowchart showing a procedure for signal restoration processing in the arrangement of the trained model 2A in FIG. 4. When the user issues an instruction to start signal restoration processing via the input interface 13, the processing circuitry 11 executes the forward propagation function 11a to start the processing shown in FIG. 5.

(Step SA1)

The processing circuitry 11 inputs the input signal y and the reliability data m.

(Step SA2)

The processing circuitry 11 generates the restored signal $x_0$ by applying the restoration function $R^{(0)}$ to the input signal y.

Figure 6:
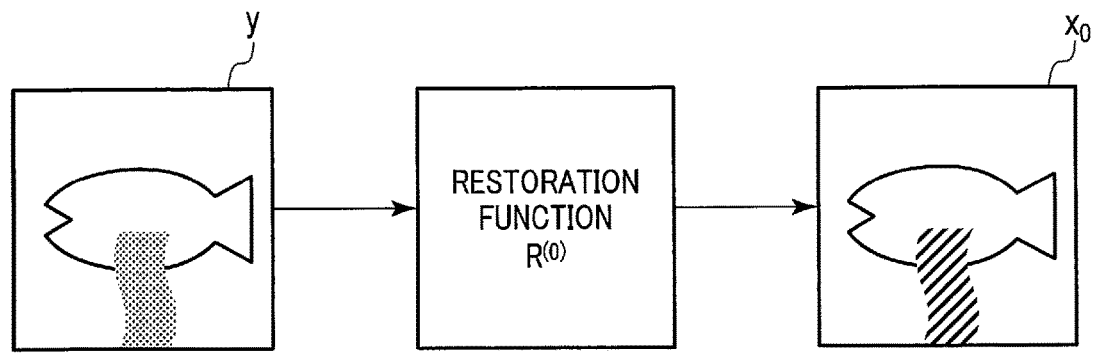
FIG. 6 is an explanatory diagram for a restoration function $R^{(0)}$ in FIG. 4.

FIG. 6 is an explanatory diagram for the restoration function $R^{(0)}$ in FIG. 4. As shown in FIG. 6, the processing circuitry 11 generates the restored signal $x_0$ by applying the restoration function $R^{(0)}$ to the input signal y.

(Step SA3)

The processing circuitry 11 substitutes "1" for a variable i.

(Step SA4)

The processing circuitry 11 generates the mask signal $ma_i$ by applying the computing function $G^{(i)}$ to the reliability data m and the restored signal $x_{i-1}$. When, for example, "1" is substituted for the variable i, the processing circuitry 11 generates a mask signal $ma_1$ by applying the computing function $G^{(1)}$ to the reliability data m and the restored signal $x_0$. For example, the computing function $G^{(1)}$ is a function of generating the mask signal $ma_1$ by performing element-wise multiplication of the reliability data m and the restored signal $x_0$.

Note that two or more computing functions $G^{(i)}$ are implemented in a trained model (that is, i≥2), different weights may be assigned to reliability data in the respective computing functions. When the three computing functions $G^{(i)}$ are implemented, a weight of "1×m" is assigned to a computing function $G^{(1)}$, a weight of "(0.8×m)+0.2" is assigned to a computing function $G^{(2)}$, and a weight of "(0.6×m)+0.4" is assigned to the computing function $G^{(3)}$. Although the weights of the computing functions $G^{(i)}$ are typically set to decrease from the input side to the output side, the function to be used are not limited to this setting.

Figure 7:
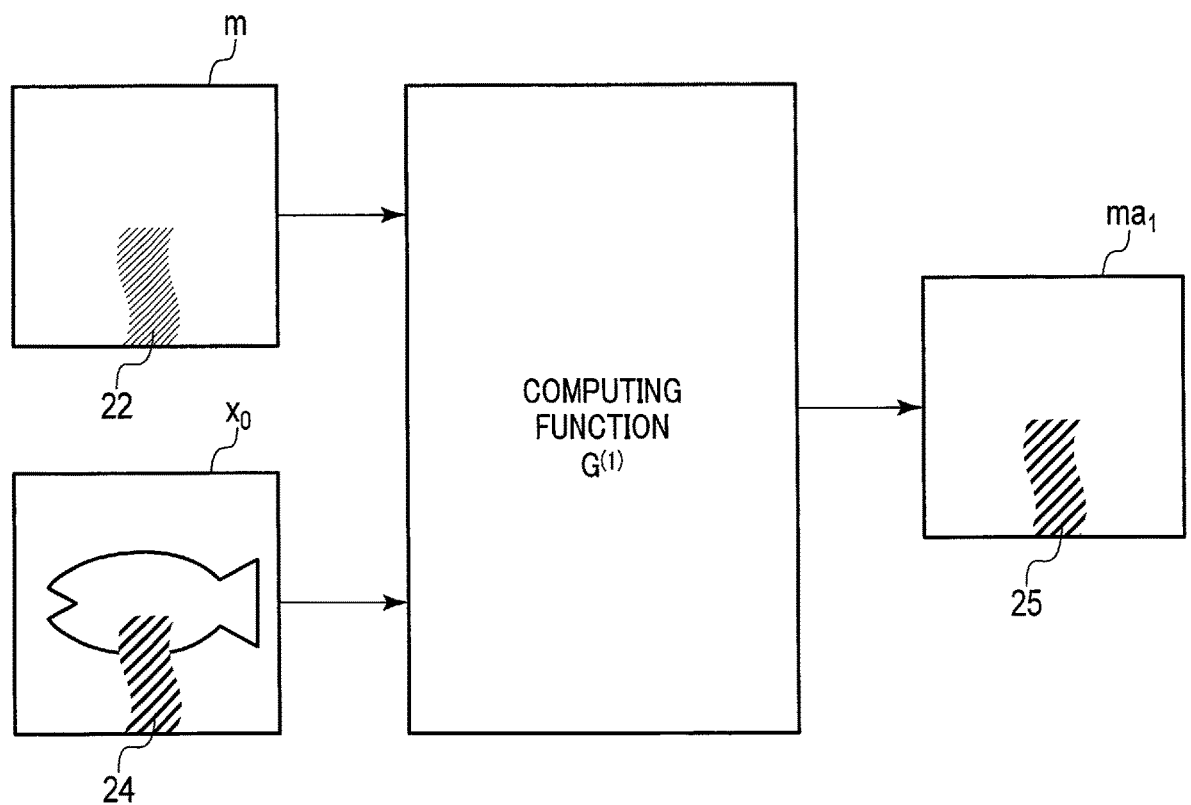
FIG. 7 is an explanatory diagram for a computing function $G^{(1)}$ in FIG. 4.

FIG. 7 is an explanatory diagram for the computing function $G^{(1)}$ in FIG. 4. As shown in FIG. 7, the processing circuitry 11 generates the mask signal $ma_1$ by applying the computing function $G^{(1)}$ to the reliability data m and restored signal $x_0$. More specifically, the processing circuitry 11 generates the mask signal $ma_1$ by extracting only a lost portion 25 corresponding to a lost portion 24 of the restored signal $x_0$ by using the lost data 22 of the reliability data m to extract the lost portion 24.

Although the above description was made by exemplifying the computing function $G^{(1)}$, the same technique can be used for each of the computing function $G^{(2)}$ to a computing function $G^{(m)}$, as shown in FIG. 4.

(Step SA5)

The processing circuitry 11 generates the restored signal $x_i$ by applying the restoration function $R^{(i)}$ to the input signal y, the restored signal $x_{i-1}$, and the mask signal $ma_i$. When, for example, "1" is substituted for the variable i, the processing circuitry 11 generates a restored signal $x_1$ by applying the restoration function $R^{(1)}$ to the input signal y, the restored signal $x_0$, and the mask signal $ma_1$.

FIG. 8 is an explanatory diagram for the restoration function $R^{(1)}$ in FIG. 4. As shown in FIG. 8, the processing circuitry 11 generates the restored signal $x_1$ by applying the restoration function $R^{(1)}$ to the input signal y, the restored signal $x_0$, and the mask signal $ma_1$.

FIG. 9 is a block diagram showing a specific example of the arrangement of the restoration function $R^{(1)}$ in FIG. 4. As shown in FIG. 9, the restoration function $R^{(1)}$ according to the first embodiment includes an input layer 31, an intermediate layer 32, and an output layer 33.

The input layer 31 inputs the input signal y, the restored signal $x_0$, and the mask signal $ma_1$. For example, components (for example, signal values) of the input signal y, the restored signal $x_0$, and the mask signal $ma_1$ are input as a single input vector 310 to the input layer 31. In this case, assuming that the input signal y includes N components, the restored signal $x_0$ includes N components, and the mask signal $ma_1$ includes N components, 3·N input units are provided for the input layer 31.

The input layer 31 is divided into a range (first input range) 310a of input units for the input signal y, a range (second input range) 310b of input units for the restored signal $x_0$, and a range (third input range) 310c of input units for the mask signal $ma_1$.

The first input range 310a includes N input units to which the Ith signal value $y_I$ ($1 \leq I \leq N$) of the input signal y is input. The second input range 310b includes N input units to which a Jth signal value $x_{0\_J}$ ($1 \leq J \leq N$) of the restored signal $x_0$ is input. The third input range 310c includes N input units to which a Kth signal value $ma_{1\_K}$ ($1 \leq K \leq N$) of the mask signal $ma_1$ is input. Note that when an image is input to the restoration function $R^{(1)}$, components are pixel values.

The output layer 33 outputs the restored signal $x_1$. The restored signal $x_1$ is output from the output layer 33 in the form of a single output vector 330. The output vector 330 includes a plurality of signal values $x_{1\_J}$ ($1 \leq J \leq N$). Each signal value $x_{1\_J}$ is the signal value of each signal of the restored signal $x_1$. A range (output range) 330a of output units of the output layer 33 is limited to a range for the single restored signal $x_i$.

A combination of an input to the first input range 310a, an input to the second input range 310b, and an input to the third input range 310c is expected to remain the same at the time of application of the restoration function $R^{(1)}$ and at the time of training of the restoration function $R^{(1)}$. Assume that at the time of training of the restoration function $R^{(1)}$, an input vector is [input signal y, restored signal $x_0$, mask signal $ma_1$]. In this case, at the time of application of the restoration function $R^{(1)}$ as well, an input vector of [input signal y, restored signal $x_0$, mask signal $ma_1$]. At this time, the input vector can be set [restored signal $x_0$, input signal y, and mask signal $ma_1$]. However, an expected result may not be obtained. In addition, the sequence of the vector elements is not limited to that described above as long as the sequence of vector elements input to the input layer remains the same at the time of application of the restoration function $R^{(1)}$ and at the time of training of the restoration function $R^{(1)}$.

Although the above description was made by exemplifying the restoration function $R^{(1)}$, the same technique can be used for each of the restoration function $R^{(2)}$ to a restoration function $R^{(m)}$, as shown in FIG. 4.

(Step SA6)

The processing circuitry 11 determines whether a predetermined number "n" is substituted for the variable i. If the predetermined number "n" is substituted for the variable i (YES in step SA6), the processing circuitry 11 performs processing in step SA8. If the arbitrary number "n" is not substituted for the variable i (NO in step SA6), the processing circuitry 11 performs processing in step SA7.

(Step SA7)

The processing circuitry 11 increments the variable i. When, for example, "1" is substituted for the variable i, the processing circuitry 11 substitutes "2" for the variable i. After processing in step SA7, the process returns to step SA4.

(Step SA8)

The processing circuitry 11 outputs the restored signal $x_n$ generated by the restoration function $R^{(m)}$ as the output signal x.

Figure 10:
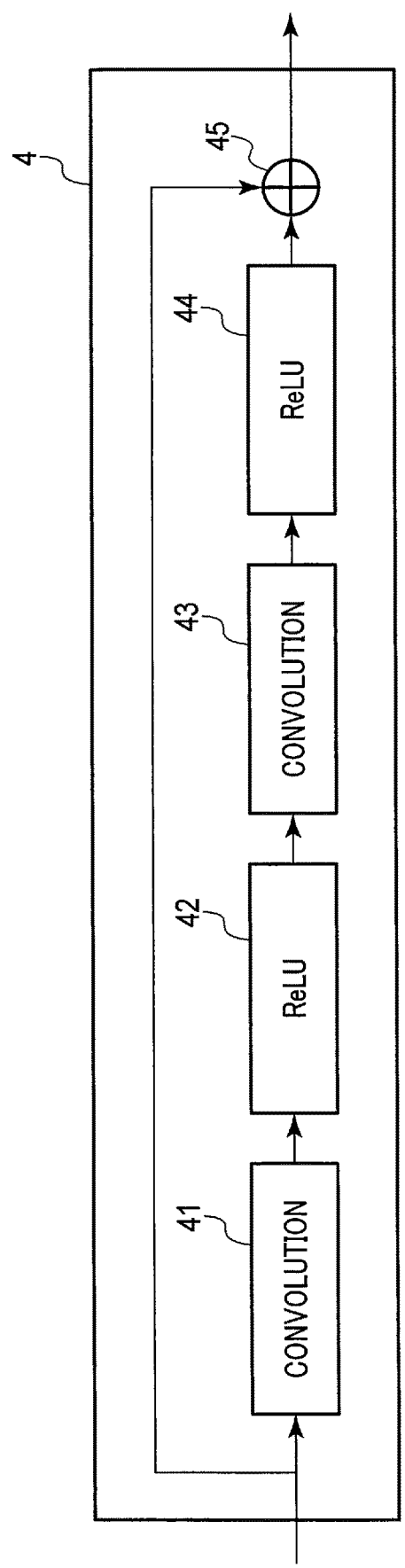
FIG. 10 is a block diagram showing an example of the arrangement of a CNN (Convolution Neural Network) according to the first embodiment.

FIG. 10 is a block diagram showing an example of the arrangement of a CNN according to the first embodiment. A CNN 4 in FIG. 10 is used for, for example, the restoration function $R^{(0)}$ and the restoration function $R^{(i)}$, and is especially suitable when an input signal and a restored signal are image data.

As shown in FIG. 10, the CNN 4 includes convolution 41, a ReLU (Rectified Linear Unit) 42, convolution 43, a ReLU 44, and an addition unit 45. Note that the CNN 4 is shown without illustration of an input layer, an output layer, and the like. In addition, the CNN 4 may not include the addition unit 45.

The convolution 41 extracts a feature from an input image by using a filter having a kernel size smaller than the matrix size of the input image. More specifically, the convolution 41 obtains the product of overlapping pixels between an input image and a filter and obtains the sum of the values of the overall filter, thereby calculating a feature amount that can be a feature of the input image.

The ReLU 42 outputs values of input signal values which are equal to or more than 0 without any change, and outputs the remaining values as 0. More specifically, the ReLU 42 outputs values of the feature amounts calculated by the convolution 41 which are equal to or more than 0 without any change, and outputs the remaining values as 0.

The convolution 43 and the ReLU 44 perform almost the same processing as that performed by the convolution 41 and the ReLU 42 except that input data differ from each other.

The addition unit 45 adds the pixel value of an input image to an output from the ReLU 44. Using the addition unit 45 allows the CNN 4 to learn a function referring to inputs to a given layer instead of training an optimal output from the given layer.

Figure 11:
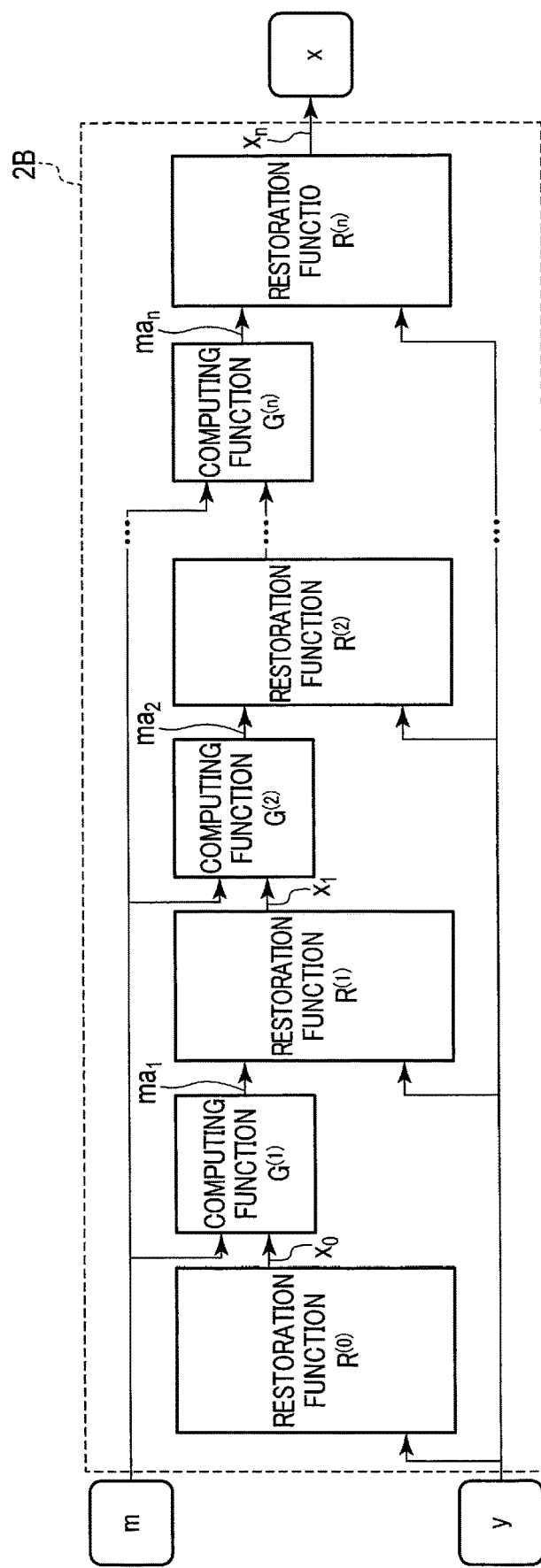
FIG. 11 is a block diagram showing another example of the arrangement of the trained model according to the first embodiment.

FIG. 11 is a block diagram showing another example of the arrangement of the trained model according to the first embodiment. As shown in FIG. 11, a trained model 2B is constituted by a process of applying the restoration function $R^{(0)}$ to arbitrary data and a process of applying a combination of the computing function $G^{(i)}$ and the restoration function $R^{(i)}$ to the arbitrary data n times (i=1 to n (n is an integer equal to or more than 1)). The trained model 2B differs from the trained model 2A in that inputs to the restoration functions $R^{(i)}$ differ from each other.

In the trained model 2B, the restoration function $R^{(i)}$ is a function of generating the restored signal $x_i$ from the input signal y and the mask signal $ma_i$. The restored signal $x_i$ is generated by, for example, applying a DNN to the input signal y and the mask signal $ma_i$. The processing circuitry 11 generates the restored signal $x_i$ by applying the restoration function $R^{(i)}$ to the input signal y and the mask signal $ma_i$.

Figure 12:
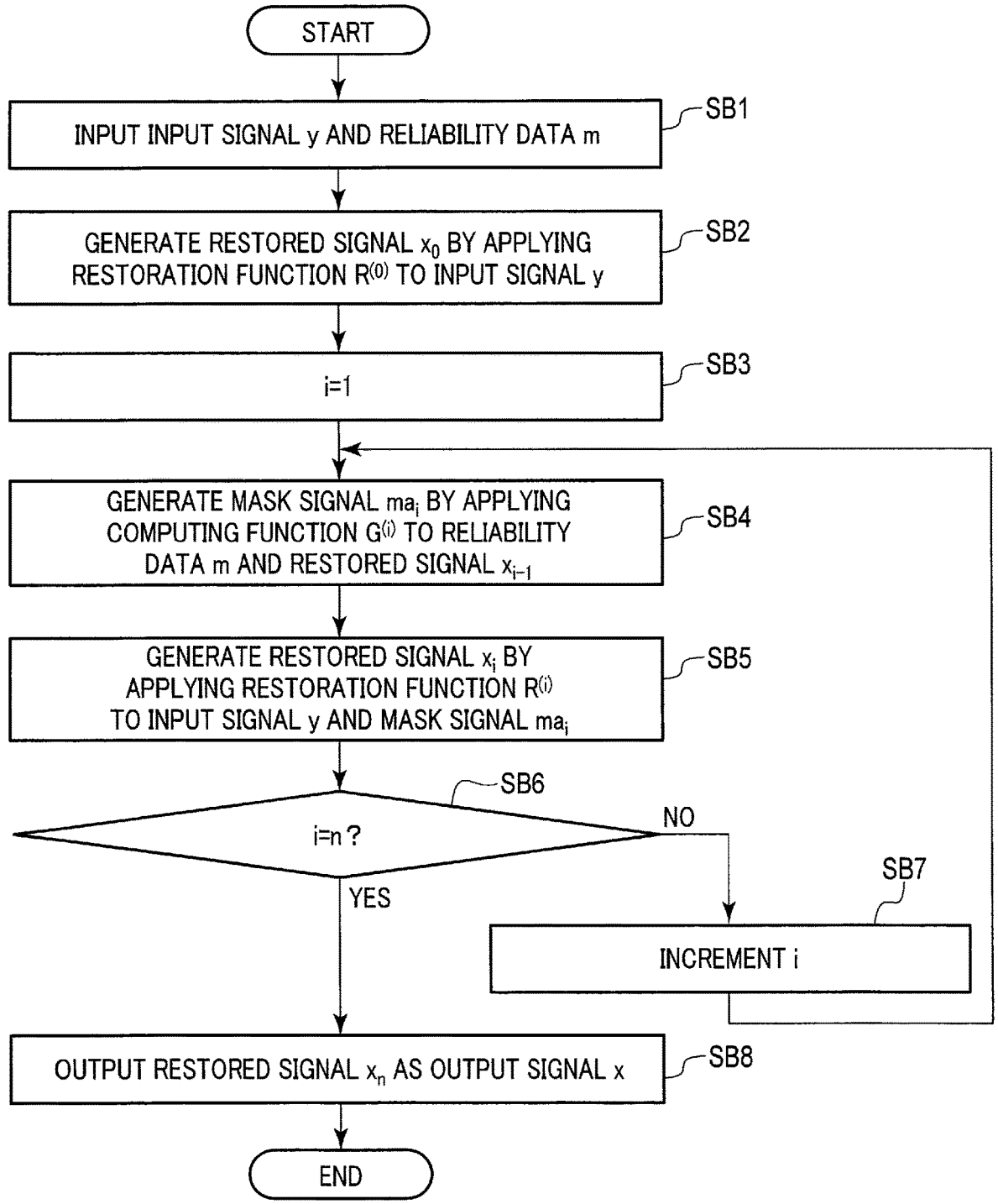
FIG. 12 is a flowchart showing a procedure for signal restoration processing in the arrangement of the trained model in FIG. 11.

FIG. 12 is a flowchart showing a procedure for signal restoration processing in the arrangement of the trained model 2B in FIG. 11. When the user issues an instruction to start signal restoration processing via the input interface 13, the processing circuitry 11 executes the forward propagation function 11a to start the processing shown in FIG. 12.

(Step SB1)
The processing circuitry 11 inputs the input signal y and the reliability data m.

(Step SB2)
The processing circuitry 11 generates the restored signal $x_0$ by applying the restoration function $R^{(0)}$ to the input signal y.

(Step SB3)
The processing circuitry 11 substitutes "1" for the variable i.

(Step SB4)
The processing circuitry 11 generates the mask signal $ma_i$ by applying the computing function $G^{(i)}$ to the reliability data m and restored signal $x_{i-1}$.

(Step SB5)
The processing circuitry 11 generates the restored signal $x_i$ by applying the restoration function $R^{(i)}$ to the input signal y and the mask signal $ma_i$.

(Step SB6)
The processing circuitry 11 determines whether a predetermined number "n" is substituted for the variable i. If the predetermined number "n" is substituted for the variable i (YES in step SB6), the processing circuitry 11 performs processing in step SB8. If the arbitrary number "n" is not substituted for the variable i (NO in step SB6), the processing circuitry 11 performs processing in step SB7.

(Step SB7)
The processing circuitry 11 increments the variable i. After processing in step SB7, the process returns to step SB4.

(Step SB8)
The processing circuitry 11 outputs the restored signal $x_n$ generated by the restoration function $R^{(n)}$ as the output signal x.

FIG. 13 is a block diagram showing another example of the arrangement of a trained model according to the first embodiment. As shown in FIG. 13, a trained model 2C is constituted by a process of applying a computing function $G^{(0)}$ to arbitrary data and a process of applying the restoration function $R^{(i)}$ to the arbitrary data n times (i=1 to n (n is an integer equal to or more than 1)). The trained model 2C differs from the trained model 2A in that it uses the computing function $G^{(0)}$ without using the computing function $G^{(i)}$.

The computing function $G^{(0)}$ is a function of generating a mask signal $ma_0$ (also called a second element-wise product signal or element-wise product signal) by performing element-wise multiplication of the input signal y and the reliability data m. At this time, conditions concerning the numbers of elements of two data are the same as those in the case of the computing function $G^{(i)}$. The processing circuitry 11 generates the mask signal $ma_0$ by applying the computing function $G^{(0)}$ to the input signal y and the reliability data m. Note that the second element-wise product signal and the element-wise product signal may be called second element-wise product data and element-wise product data, respectively.

In the trained model 2C, the restoration function $R^{(i)}$ is a function of generating the restored signal $x_i$ from the input signal y, the restored signal $x_{i-1}$, and the mask signal $ma_0$. The restored signal $x_i$ is generated by, for example, applying a DNN to the input signal y, the restored signal $x_{i-1}$, and the mask signal $ma_0$. The processing circuitry 11 generates the restored signal $x_i$ by applying the restoration function $R^{(i)}$ to the input signal y, the restored signal $x_{i-1}$, and the mask signal $ma_0$.

Figure 14:
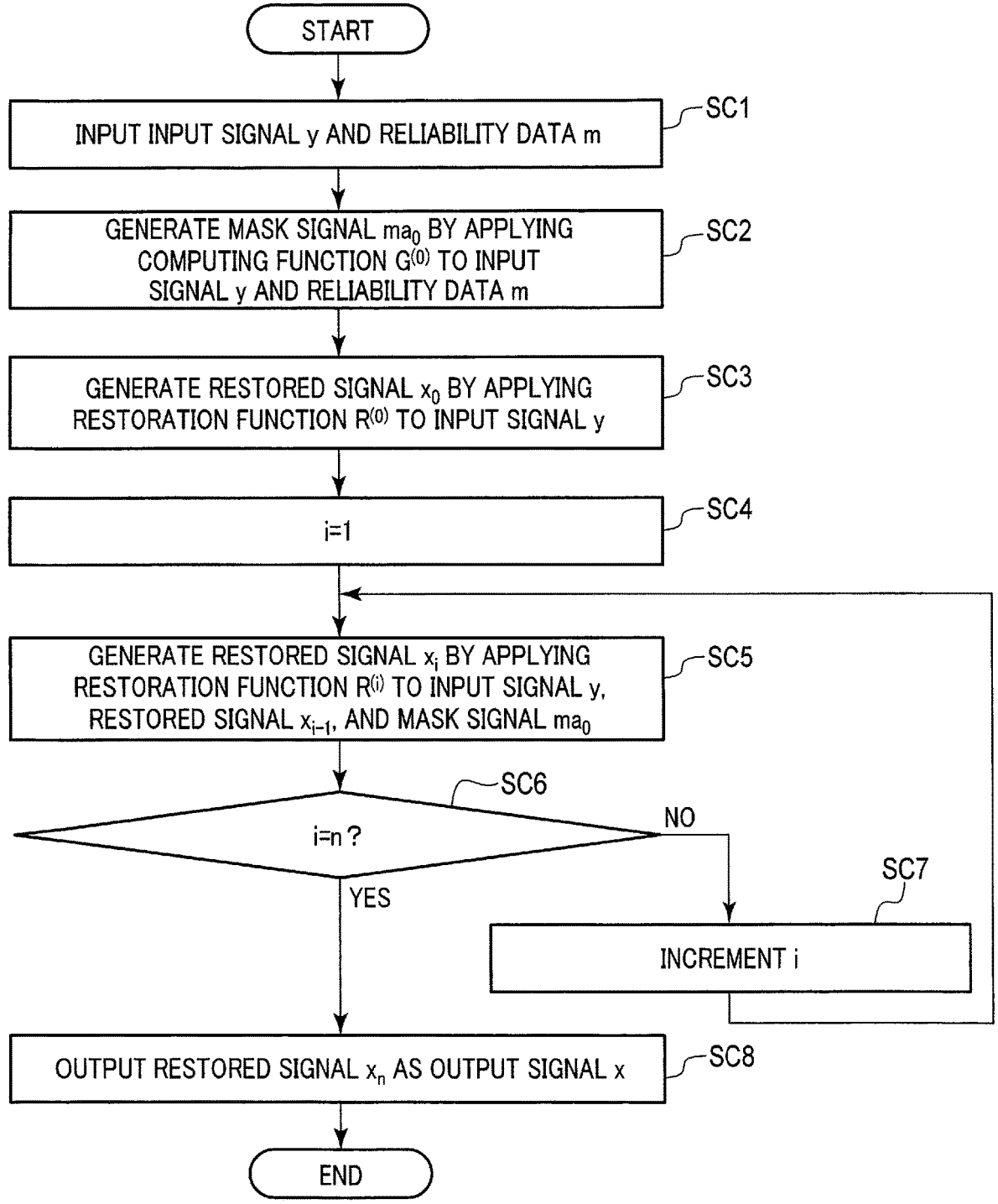
FIG. 14 is a flowchart showing a procedure for signal restoration processing in the arrangement of the trained model in FIG. 13.

FIG. 14 is a flowchart showing a procedure for signal restoration processing in the arrangement of the trained model 2C in FIG. 13. When the user issues an instruction to start signal restoration processing via the input interface 13, the processing circuitry 11 executes the forward propagation function 11a to start the processing shown in FIG. 14.

(Step SC1)
The processing circuitry 11 inputs the input signal y and the reliability data m.

(Step SC2)
The processing circuitry 11 generates the mask signal $ma_0$ by applying the computing function $G^{(0)}$ to the input signal y and the reliability data m.

(Step SC3)
The processing circuitry 11 generates the restored signal $x_0$ by applying the restoration function $R^{(0)}$ to the input signal y.

(Step SC4)
The processing circuitry 11 substitutes "1" for the variable i.

(Step SC5)
The processing circuitry 11 generates the restored signal $x_i$ by applying the restoration function $R^{(i)}$ to the input signal y, the restored signal $x_{i-1}$, and the mask signal $ma_0$.

(Step SC6)
The processing circuitry 11 determines whether a predetermined number "n" is substituted for the variable i. If the predetermined number "n" is substituted for the variable i (YES in step SC6), the processing circuitry 11 performs processing in step SC8. If the arbitrary number "n" is not substituted for the variable i (NO in step SC6), the processing circuitry 11 performs processing in step SC7.

(Step SC7)
The processing circuitry 11 increments the variable i. After processing in step SC7, the process returns to step SC5.

(Step SC8)
The processing circuitry 11 outputs the restored signal $x_n$ generated by the restoration function $R^{(n)}$ as the output signal x.

FIG. 15 is a block diagram showing another example of the arrangement of the trained model according to the first embodiment. As shown in FIG. 15, a trained model 2D is constituted by a process of applying the computing function $G^{(0)}$ to arbitrary data, a process of applying the restoration function $R^{(0)}$ to the arbitrary data, and a process of applying a combination of the computing function $G^{(i)}$ and the restoration function $R^{(i)}$ to the arbitrary data n times (i=1 to n (n is an integer equal to or more than 1)). The trained model 2D differs from the trained model 2A in that it further uses the computing function $G^{(0)}$. Note that the computing function $G^{(0)}$ in FIG. 15 functions in the same manner as the computing function $G^{(0)}$ in FIG. 13, and hence a description of the computing function $G^{(0)}$ will be omitted.

In the trained model 2D, the restoration function $R^{(i)}$ generates the restored signal $x_i$ from the input signal y, the mask signal $ma_i$, and the mask signal $ma_O$. The restored signal $x_i$ is generated by, for example, applying a DNN to the input signal y, the mask signal $ma_i$, and the mask signal $ma_O$. The processing circuitry 11 generates the restored signal $x_i$ by applying the restoration function $R^{(i)}$ to the input signal y, the mask signal $ma_i$, and the mask signal $ma_O$.

Figure 16:
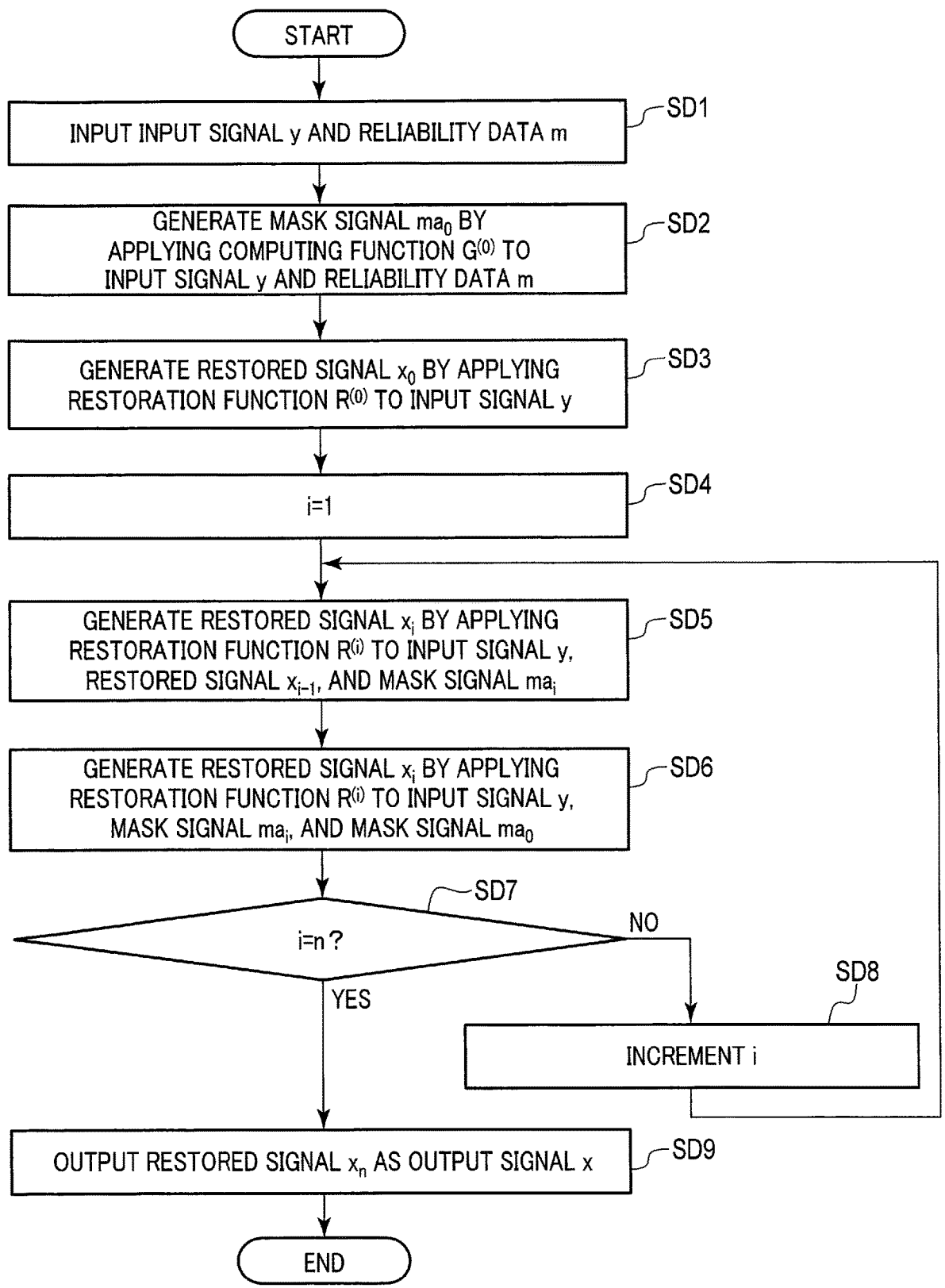
FIG. 16 is a flowchart showing a procedure for signal restoration processing in the arrangement of the trained model in FIG. 15.

FIG. 16 is a flowchart showing a procedure for signal restoration processing in the arrangement of the trained model 2D in FIG. 15. When the user issues an instruction to start signal restoration processing via the input interface 13, the processing circuitry 11 executes the forward propagation function 11a to start the processing shown in FIG. 16.

(Step SD1)
The processing circuitry 11 inputs the input signal y and the reliability data m.

(Step SD2)
The processing circuitry 11 generates the mask signal $ma_O$ by applying the computing function $G^{(O)}$ to the input signal y and the reliability data m.

(Step SD3)
The processing circuitry 11 generates the restored signal $x_0$ by applying the restoration function $R^{(o)}$ to the input signal y.

(Step SD4)
The processing circuitry 11 substitutes "1" for the variable i.

(Step SD5)
The processing circuitry 11 generates the mask signal $ma_i$ by applying the computing function $G^{(i)}$ to the reliability data m and the restored signal $x_{i-1}$.

(Step SD6)
The processing circuitry 11 generates the restored signal $x_i$ by applying the restoration function $R^{(i)}$ to the input signal y, the mask signal $ma_i$, and the mask signal $ma_O$.

(Step SD7)
The processing circuitry 11 determines whether a predetermined number "n" is substituted for the variable i. If the predetermined number "n" is substituted for the variable i (YES in step SD7), the processing circuitry 11 performs processing in step SD9. If the arbitrary number "n" is not substituted for the variable i (NO in step SD7), the processing circuitry 11 performs processing in step SD8.

(Step SD8)
The processing circuitry 11 increments the variable i. After the processing in step SD8, the process returns to step SD5.

(Step SD9)
The processing circuitry 11 outputs the restored signal $x_n$ generated by the restoration function $R^{(n)}$ as the output signal x.

Figure 17:
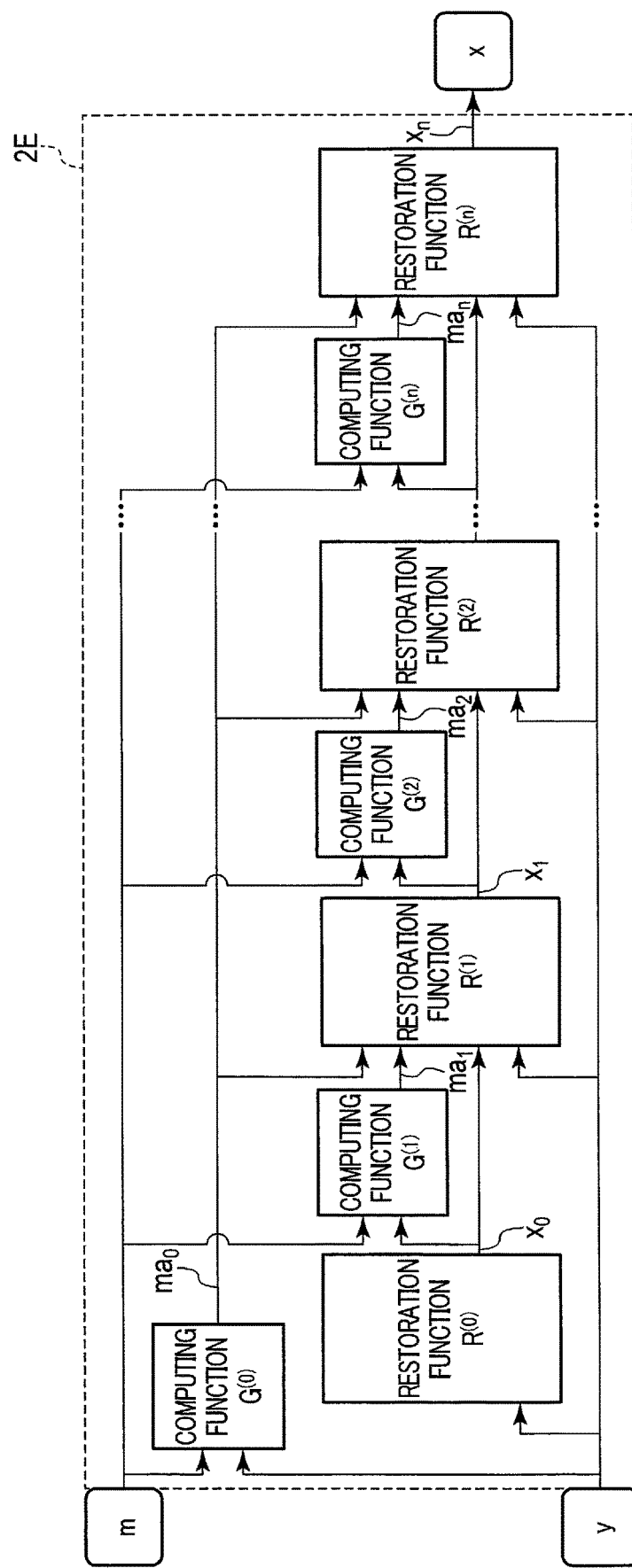
FIG. 17 is a block diagram showing another example of the arrangement of the trained model according to the first embodiment.

FIG. 17 is a block diagram showing another example of the arrangement of the trained model according to the first embodiment. As shown in FIG. 17, a trained model 2E is constituted by a process of applying the computing function $G^{(O)}$ to arbitrary data, a process of applying the restoration function $R^{(O)}$ to the arbitrary data, and a process of applying a combination of the computing function $G^{(i)}$ and the restoration function $R^{(i)}$ to the arbitrary data n times (i=1 to n (n is an integer equal to or more than 1)). The trained model 2E differs from the trained model 2D in that inputs to the restoration functions $R^{(i)}$ differ from each other.

In the trained model 2E, the restored signal $x_i$ is generated from the input signal y, the restored signal $x_{i-1}$, the mask signal $ma_i$, and the mask signal $ma_O$. The restored signal $x_i$ is generated by, for example, applying a DNN to the input signal y, the restored signal $x_{i-1}$, the mask signal $ma_i$, and the mask signal $ma_O$. The processing circuitry 11 generates the restored signal $x_i$ by applying the restoration function $R^{(i)}$ to the input signal y, the restored signal $x_{i-1}$, the mask signal $ma_i$, and the mask signal $ma_O$.

FIG. 18 is a flowchart showing a procedure for signal restoration processing in the arrangement of the trained model 2E in FIG. 17. When the user issues an instruction to start signal restoration processing via the input interface 13, the processing circuitry 11 executes the forward propagation function 11a to start the processing shown in FIG. 18.

(Step SE1)
The processing circuitry 11 inputs the input signal y and the reliability data m.

(Step SE2)
The processing circuitry 11 generates the mask signal $ma_O$ by applying the computing function $G^{(O)}$ to the input signal y and the reliability data m.

(Step SE3)
The processing circuitry 11 generates the restored signal $x_0$ by applying the restoration function $R^{(O)}$ to the input signal y.

(Step SE4)
The processing circuitry 11 substitutes "1" for the variable i.

(Step SE5)
The processing circuitry 11 generates the mask signal $ma_i$ by applying the computing function $G^{(i)}$ to the reliability data m and the restored signal $x_{i-1}$.

(Step SE6)
The processing circuitry 11 generates the restored signal $x_i$ by applying the restoration function $R^{(i)}$ to the input signal y, the restored signal $x_{i-1}$, the mask signal $ma_i$, and the mask signal $ma_O$.

(Step SE7)
The processing circuitry 11 determines whether a predetermined number "n" is substituted for the variable i. If the predetermined number "n" is substituted for the variable i (YES in step SE7), the processing circuitry 11 performs processing in step SE9. If the arbitrary number "n" is not substituted for the variable i (NO in step SE7), the processing circuitry 11 performs processing in step SE8.

(Step SE8)
The processing circuitry 11 increments the variable i. After the processing in step SE8, the process returns to step SE5.

(Step SE9)
The processing circuitry 11 outputs the restored signal $x_n$ generated by the restoration function $R^{(n)}$ as the output signal x.

Figure 19:
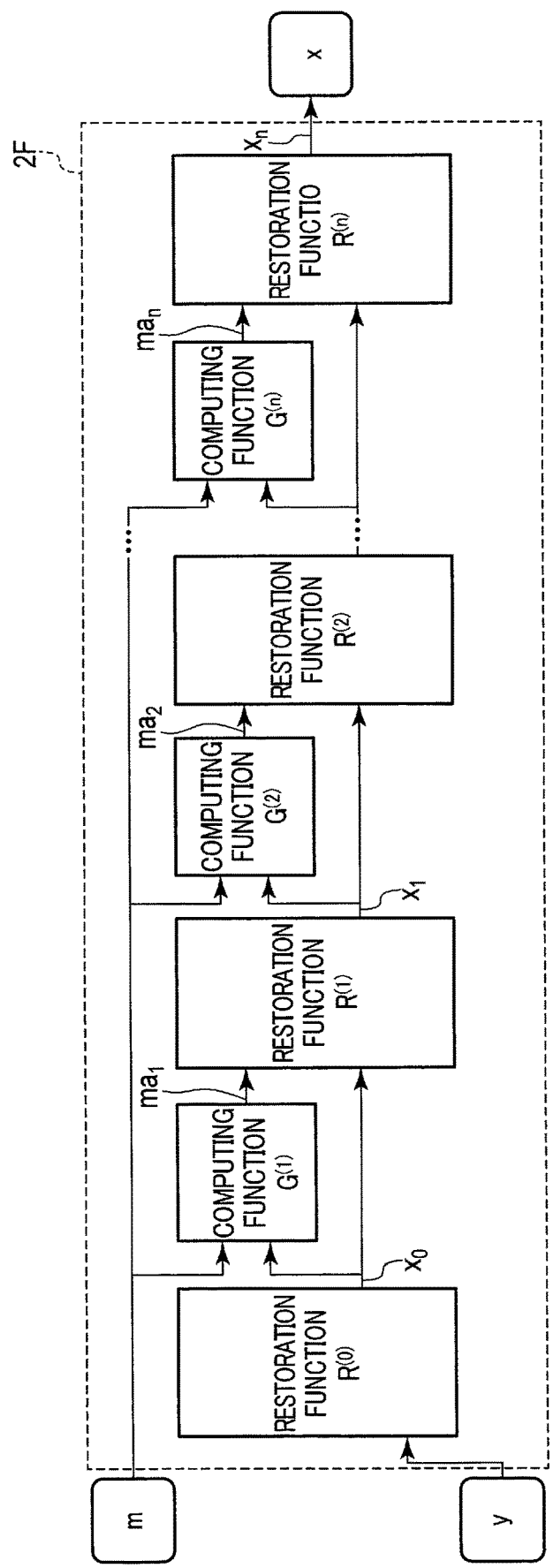
FIG. 19 is a block diagram showing another example of the arrangement of the trained model according to the first embodiment.

FIG. 19 is a block diagram showing another example of the arrangement of the trained model according to the first embodiment. As shown in FIG. 19, a trained model 2F differs from the trained model 2A in that inputs to the restoration functions $R^{(i)}$ differ from each other.

In the trained model 2F, the restoration function $R^{(i)}$ generates the restored signal $x_i$ from the restored signal $x_{i-1}$ and the mask signal $ma_i$. The restored signal $x_i$ is generated by, for example, applying a DNN to the restored signal $x_{i-1}$ and the mask signal $ma_i$. The processing circuitry 11 generates the restored signal $x_i$ by applying the restoration function $R^{(i)}$ to the restored signal $x_{i-1}$ and the mask signal $ma_i$.

FIG. 20 is a block diagram showing another example of the arrangement of the trained model according to the first embodiment. As shown in FIG. 20, a trained model 2G differs from the trained model 2C in that inputs to the restoration functions $R^{(i)}$ differ from each other.

In the trained model 2G, the restoration function $R^{(i)}$ generates the restored signal $x_i$ from the restored signal $x_{i-1}$ and the mask signal $ma_O$. The restored signal $x_i$ is generated by, for example, applying a DNN to the restored signal $x_{i-1}$ and the mask signal $ma_O$. The processing circuitry 11 generates the restored signal $x_i$ by applying the restoration function $R^{(i)}$ to the restored signal $x_{i-1}$ and the mask signal $ma_O$.

FIG. 21 is a block diagram showing another example of the arrangement of the trained model according to the first embodiment. As shown in FIG. 21, a trained model 2H differs from the trained model 2E in that inputs to the restoration functions $R^{(i)}$ differ from each other.

In the trained model 2H, the restoration function $R^{(i)}$ generates the restored signal $x_i$ from the restored signal $x_{i-1}$, the mask signal $ma_i$, and the mask signal $ma_O$. The restored signal $x_i$ is generated by, for example, applying a DNN to the restored signal $x_{i-1}$, the mask signal $ma_i$, and the mask signal $ma_O$. The processing circuitry 11 generates the restored signal $x_i$ by applying the restoration function $R^{(i)}$ to the restored signal $x_{i-1}$, the mask signal $ma_i$, and the mask signal $ma_O$.

Figure 22:
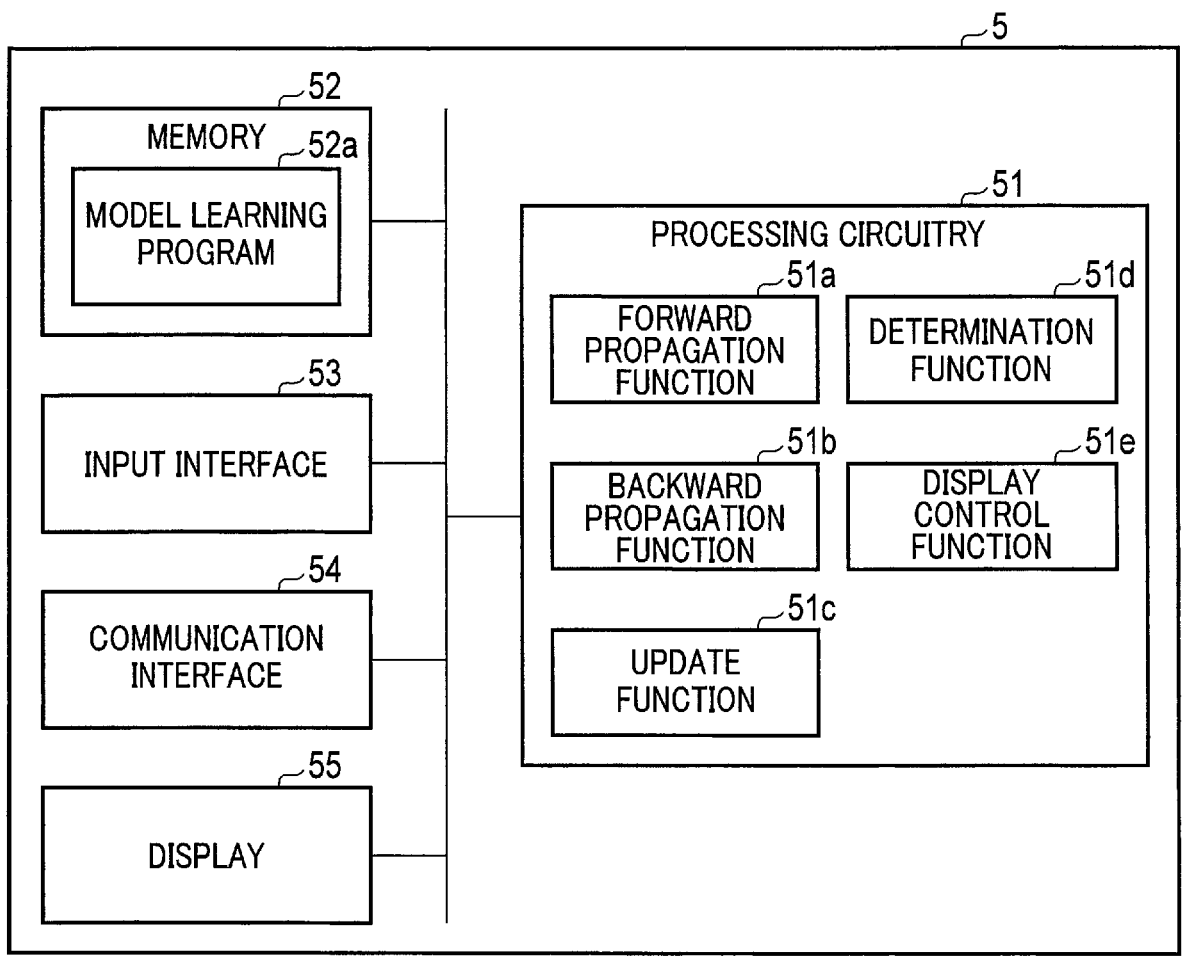
FIG. 22 is a block diagram showing an example of the arrangement of a model training apparatus according to the first embodiment.

FIG. 22 is a block diagram showing an example of the arrangement of a model training apparatus according to the first embodiment. A model training apparatus 5 in FIG. 22 includes, as hardware resources, processing circuitry 51, a memory 52, an input interface 53, a communication interface 54, and a display 55. The processing circuitry 51, the memory 52, the input interface 53, the communication interface 54, and the display 55 are connected to each other via a bus.

The processing circuitry 51 includes a processor such as a CPU or GPU. The processor executes a forward propagation function 51a, a backward propagation function 51b, an update function 51c, a determination function 51d, and a display control function 51e by activating the DNN restoration program installed in the memory 52 or the like. Note that the forward propagation function 51a, the backward propagation function 51b, the update function 51c, the determination function 51d, and the display control function 51e need not always be implemented by single processing circuitry. Processing circuitry may be constituted by a plurality of independent processors, and each processor execute a program to implement the forward propagation function 51a, the backward propagation function 51b, the update function 51c, the determination function 51d, and the display control function 51e.

When executing the forward propagation function 51a, the processing circuitry 51 propagates forward an input signal and reliability data to a DNN and generates an estimated output signal corresponding to the input signal. Note that the DNN is a DNN that has not trained any parameters or is training parameters. In addition, although the DNN uses one of the arrangements of the trained model 2A to the trained model 2H described above, the parameters of the respective functions are initial values or not optimized. Note that an estimated output signal may be called estimated output signal data.

When executing the backward propagation function 51b, the processing circuitry 51 propagates backward an error to the DNN and calculates a gradient vector. The error is defined by the difference between the estimated output signal calculated by the forward propagation function 51a and a correct output signal. Note that the correct output signal may be called correct output signal data.

When executing the update function 51c, the processing circuitry 51 updates DNN parameters based on the gradient vector calculated by the backward propagation function 51b. More specifically, the processing circuitry 51 updates parameters so as to approximate the estimated output signal to the correct output signal. As an update method, for example, SGD (Stochastic Gradient Decent) or Adam (Adaptive Moment Estimation) can be used.

When executing the determination function 51d, the processing circuitry 51 determines whether termination conditions for a training process are satisfied. The user can arbitrarily set termination conditions via an input device or the like.

When executing the display control function 51e, the processing circuitry 51 displays various information on the display 55. For example, the processing circuitry 51 displays training data and training results on the display 55.

The memory 52 is a storage device such as a ROM, RAM, HDD, SSD, or integrated circuit storage device, which stores various information. The memory 52 stores, for example, a model training program 52a for DNN training. The memory 52 may be a portable storage medium such as a CD, DVD, or flash memory or a driver that reads and writes various information from and in a semiconductor memory element such as a RAM, other than the above storage device. The memory 52 may be installed in another computer connected to the model training apparatus 5 via a network.

The input interface 53 accepts various types of input operations from the user, converts the accepted input operations into electrical signals, and outputs them to the processing circuitry 51. More specifically, the input interface 53 is connected to an input device such as a mouse, keyboard, trackball, switches, buttons, joystick, touch pad, and touch panel display. The input interface 53 outputs an electrical signal corresponding to an input operation with respect to the input device to the processing circuitry 51. An input device connected to the input interface 53 may be an input device provided for another computer connected via a network.

The communication interface 54 is an interface for performing data communication with another computer such as a medical imaging apparatus or distance image photographing apparatus.

The display 55 displays various information in accordance with the display control function 51e of the processing circuitry 51. For example, the display 55 displays training data and training results. In addition, the display 55 outputs, for example, a GUI for accepting various types of operations from the user. For example, as the display 55, a liquid crystal display, CRT display, organic EL display, plasma display, or another arbitrary display can be used as needed.

Note that the model training apparatus 5 in FIG. 22 need not include the input interface 53 and the display 55. When not having the input interface 53 and the display 55, the model training apparatus 5 may be implemented by an integrated circuit such as an ASIC or FPGA, and the communication interface 54 may have both the functions of the input interface 13 and the output interface 14 described above. When the model training apparatus 5 is an ASIC, the processing circuitry 51 is a circuit element or a combination of logic circuits designed to execute the forward propagation function 51a, the backward propagation function 51b, the update function 51c, and the determination function 51d.

Figure 23:
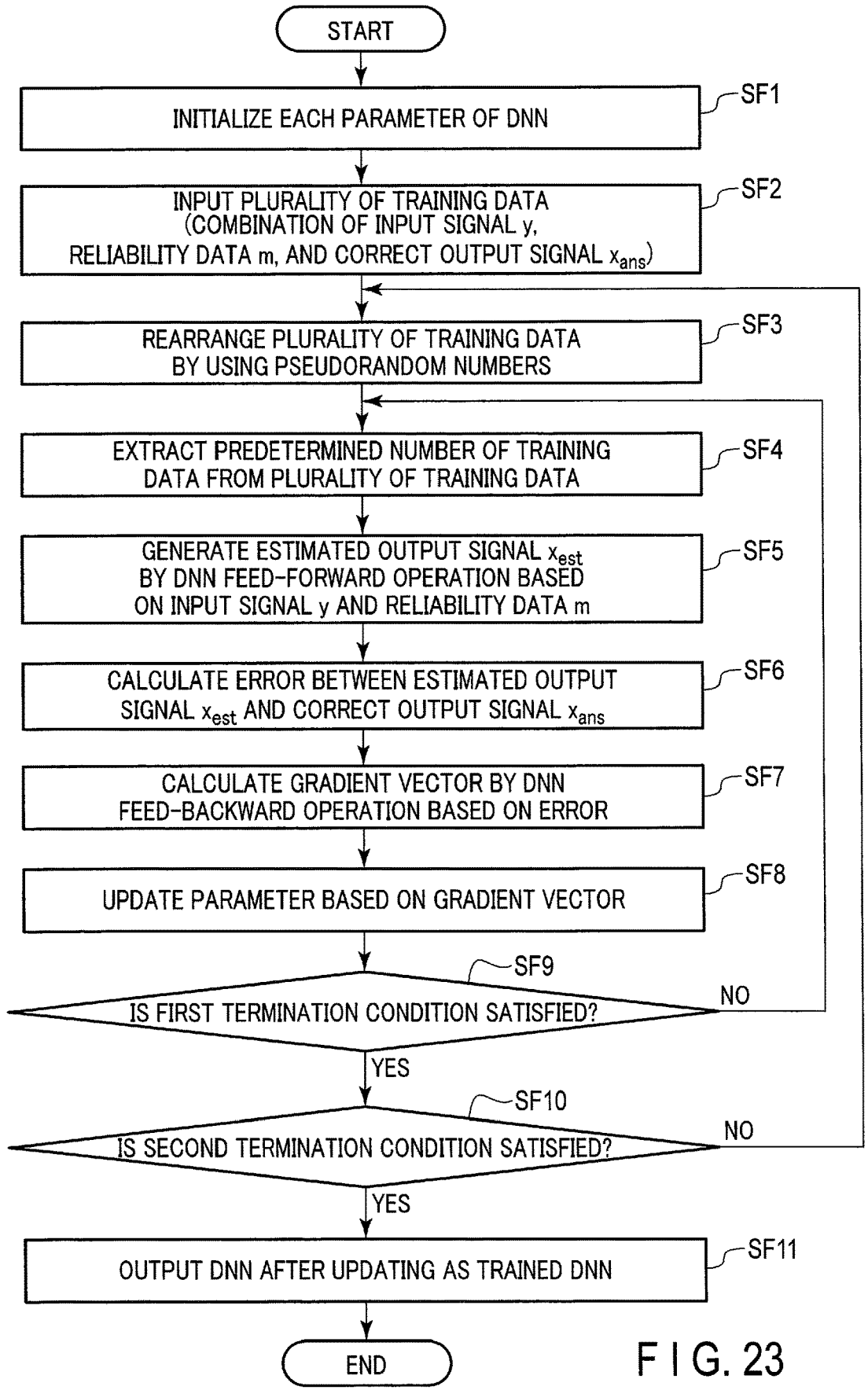
FIG. 23 is a flowchart showing an example of a model training process which the processing circuitry of the model training apparatus in FIG. 22 executes in accordance with a model training program.

FIG. 23 is a flowchart showing an example of a model training process which the processing circuitry of the model training apparatus in FIG. 22 executes in accordance with a model training program. The processing in FIG. 23 is started by the processing circuitry 51 when it executes the model training program 52a in response to the reception of an instruction to start a model training process from the user or the like. Note that a plurality of training data are stored in, for example, an external storage device such as the memory 52.

(Step SF1)

The processing circuitry 51 initializes each parameter of the DNN. For the initialization of parameters, for example, pseudorandom numbers can be used.

(Step SF2)

The processing circuitry 51 inputs a plurality of training data (a combination of the input signal y, the reliability data m, and a correct output signal $x_{ans}$). The correct output signal $x_{ans}$ is a desired output signal to be output from DNN upon inputting of the input signal y and the reliability data m.

(Step SF3)

The processing circuitry 51 rearranges a plurality of training data by using pseudorandom numbers. More specifically, the processing circuitry 51 rearranges a plurality of training data in the order of generation by pseudorandom numbers.

(Step SF4)

The processing circuitry 51 extracts a predetermined number of training data from the plurality of training data. In this case, a predetermined number is called a mini-batch size, and a set of extracted training data is called a mini-batch. In other words, the processing circuitry 51 extracts a mini-batch from a plurality of training data.

(Step SF5)

When executing the forward propagation function 51a, the processing circuitry 51 generates an estimated output signal $x_{est}$ by the feed-forward operation of the DNN based on the input signal y and the reliability data m.

(Step SF6)

When executing the backward propagation function 51b, the processing circuitry 51 calculates the error between the estimated output signal $x_{est}$ generated in step SF5 and the correct output signal $x_{ans}$ input in step SF2. More specifically, the processing circuitry 51 calculates the error by subtracting the estimated output signal $x_{est}$ from the correct output signal $x_{ans}$.

(Step SF7)

The processing circuitry 51 calculates a gradient vector by the feed-backward operation of the DNN based on the error calculated in step SF6.

(Step SF8)

When executing the update function 51c, the processing circuitry 51 updates parameters based on the gradient vector calculated in step SF7.

(Step SF9)

When executing the determination function 51d, the processing circuitry 51 determines whether a first termination condition is satisfied. For example, the first termination condition may be set by extracting all mini-batches from a plurality of training data.

If the processing circuitry 51 determines in step SF9 that the first termination condition is not satisfied (NO in step SF9), the processing circuitry 51 repeats processing from step SF4 to step SF9 by using the same mini-batch or another mini-batch.

If the processing circuitry 51 determines in step SF9 that the first termination condition is satisfied (YES in step SF9), the process advances to step SF10.

(Step SF10)

When executing the determination function 51d, the processing circuitry 51 determines whether a second termination condition is satisfied. The second termination condition may be set such that, for example, the number of repetitions (to be also referred to as an epoch number) has reached a predetermined number.

If the processing circuitry 51 determines in step SF10 that the second termination condition is not satisfied (NO in step SF10), the processing circuitry 51 repeats processing from step SF3 to step SF9.

If the processing circuitry 51 determines in step SF10 that the second termination condition is satisfied (YES in step SF10), the process advances to step SF11.

(Step SF11)

The processing circuitry 51 outputs the DNN after updating as a trained DNN. The trained DNN is stored in, for example, the memory 52 or an external storage device.

As described above, the model training program 52a according to this embodiment causes the model training apparatus 5 to execute at least the forward propagation function 51a and the update function 51c. The forward propagation function 51a generates an estimated output signal by applying an input signal and reliability data to a multilayer network including an input layer that inputs an input signal and reliability data concerning the input signal, an output layer that outputs an output signal corresponding to the input signal, and at least one intermediate layer that is provided between the input layer and the output layer. The update function 51c updates DNN parameters so as to approximate an estimated output signal to a correct output signal.

With the above arrangement, the model training program 52a according to this embodiment learns DNN parameters by using not only an input signal but also reliability data to output an output signal obtained by restoring a signal lost portion of the input signal. This allows the model training program 52a according to the embodiment to use a larger amount of information that is not included in an input signal when training parameters. This makes it possible to improve the restoration accuracy of a signal restored by the trained model as compared with the case of using only an input signal.

As described above, the signal restoration apparatus 1 according to this embodiment includes the processing circuitry 11. The processing circuitry 11 generates initial restored signal data by applying a first restoration function to input signal data, and generates first element-wise product signal data by calculating the element-wise product of the initial restored signal data and reliability data representing the degree of degradation included in the input signal. The processing circuitry 11 generates restored signal data by applying a second restoration function to at least one of the input signal data and the initial restored signal data and the first element-wise product signal data.

The processing circuitry 11 further generates second element-wise product signal data by calculating the element-wise product of the input signal data and the reliability data. Upon generating the second element-wise product signal data, the processing circuitry 11 generates restored signal data by applying the second restoration function to at least one of the input signal data and the initial restored signal data, the first element-wise product signal data, and the second element-wise product signal data.

Alternatively, the processing circuitry 11 generates initial restored signal data by applying the first restoration function to the input signal data, and generates element-wise product signal data by calculating the element-wise product of the input signal data and reliability data representing the degree of degradation included in the input signal data. The processing circuitry 11 then generates restored signal data by applying the second restoration function to the initial restored signal data and the element-wise product signal data.

The processing circuitry 11 may further generate restored signal data by applying the second restoration function to the input signal data, the initial restored signal data, and the element-wise product signal data.

The above second restoration function may be formed from a deep neural network, convolution neural network, or recurrent neural network.

With the above arrangement, using reliability data allows the signal restoration apparatus 1 according to this embodiment to perform signal restoration by using a larger amount of information that is not included in input signal data. Accordingly, the signal restoration apparatus 1 can improve the restoration accuracy of a signal as compared with the case of using only input signal data. In addition, because reliability data is only required to include reliability information concerning input signal data, the data format of the reliability data does not necessarily match that of the input signal data. This enables the signal restoration apparatus 1 to reduce the trouble of the user in preparing desired data.

As a modification of the first embodiment, when the technical idea of the model training apparatus 5 is to be implemented by cloud computing or the like, a server on a network includes, for example, the processing circuitry 51 and the memory 52 in the arrangement in FIG. 22. In this case, this technical idea is implemented by installing programs for executing the respective functions of the processing circuitry 51 in the processing circuitry 51 of the server and expanding the programs in the memory 52.

Second Embodiment

FIG. 24 is a block diagram showing an example of the arrangement of a medical image diagnostic apparatus according to the second embodiment. A medical image diagnostic apparatus 100 in FIG. 24 includes the signal restoration apparatus 1 according to the first embodiment and a medical imaging apparatus 6. For example, the medical imaging apparatus 6 corresponds to a gantry, and the signal restoration apparatus 1 corresponds to a console connected to the gantry. Note that the signal restoration apparatus 1 may be provided on the gantry of the medical image diagnostic apparatus 100 or implemented by another constituent element. When, for example, the medical image diagnostic apparatus 100 is an MRI (Magnetic Resonance Imaging) apparatus, another constituent element can be a computer other than the console or a dedicated computing device installed in a machine room.

The medical imaging apparatus 6 generates a medical signal corresponding to an input signal as a processing target. A medical signal according to this embodiment conceptually includes raw data acquired by medical imaging of an object with the medical imaging apparatus 6 or another medical imaging apparatus and medical image data generated by applying image restoration processing to the raw data. Note that a medical signal may be called medical signal data. In addition, the signal restoration apparatus 1 may generate medical image data by applying image restoration processing to raw data. Medical image data corresponds to, for example, an MR (Magnetic Resonance) image, CT image, X-ray image, or the like.

A signal restoration apparatus that handles a medical signal as an input signal may be called a medical signal processing apparatus. The medical signal processing apparatus may be a computer mounted in the medical image diagnostic apparatus 100 equipped with the medical imaging apparatus 6, a computer communicably connected to the medical image diagnostic apparatus 100 via a cable or network, or a computer independent of the medical image diagnostic apparatus 100.

The medical imaging apparatus 6 can be any type of modality apparatus as long as it can generate medical signals. For example, a medical imaging apparatus 3 according to this embodiment may be a single modality apparatus such as an MRI (Magnetic Resonance Imaging) apparatus, an X-ray CT (Computer Tomography) apparatus, an X-ray diagnostic apparatus, a PET (Positron Emission Tomography) apparatus, a SPECT (Single Photon Emission CT) apparatus, or an ultrasonic diagnostic apparatus or a composite modality apparatus such as a PET/CT apparatus, a SPECT/CT apparatus, a PET/MRI apparatus, or a SPECT/MRI apparatus.

In other words, the medical imaging apparatus 6 acquires raw data concerning an object by performing medical imaging of the object based on an imaging principle corresponding to the modality apparatus type of the medical imaging apparatus 6. The acquired raw data is transmitted to the signal restoration apparatus 1. For example, the raw data is k-space data when the medical imaging apparatus 6 is an MRI apparatus, projection data or sinogram data when the medical imaging apparatus 6 is a CT apparatus, echo data when the medical imaging apparatus 6 is an ultrasonic diagnostic apparatus, coincidence data or sinogram data when the medical imaging apparatus 6 is a PET apparatus, or projection data or sinogram data when the medical imaging apparatus 6 is a SPECT apparatus. Note that the medical imaging apparatus 6 is an example of an implementation means for a medical imaging unit.

(Application Example in MRI Apparatus)

When the medical imaging apparatus 6 is the gantry of an MRI apparatus, the gantry repeats application of a gradient magnetic field via a gradient magnetic field coil and application of an RF pulse via a transmission coil under application of a static magnetic field via a static field magnet. MR signals are emitted from an object upon application of RF pulses. The emitted MR signals are received via a reception coil. Reception circuitry applies signal processing such as A/D conversion to the received MR signals. The MR signals after the A/D conversion correspond to k-space data. The k-space data is transmitted as raw data to the signal restoration apparatus 1.

The following is a case in which FFT (Fast Fourier Transform) is used when an MR image is generated from k-space data, and IFFT (Inverse Fast Fourier Transform) is used when an MR image is converted into k-space data. FFT and IFFT are used differently depending on the definition of a k-space. Accordingly, when IFFT is to be used to generate an MR image from k-space data and FFT is to be used to convert an MR image into k-space data, the terms "FFT" and "IFFT" may be respectively replaced with "IFFT" and "FFT". Note that a method of generating MR images from k-space data or a method of converting MR images into k-space data is not limited by FFT and IFFT.

Figure 25:
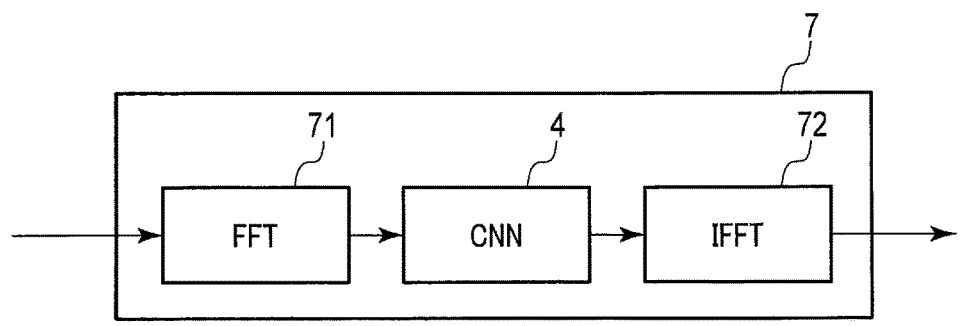
FIG. 25 is a block diagram showing an example of the arrangement of a restoration function in a trained model when the medical imaging apparatus in FIG. 24 is an MRI (Magnetic Resonance Imaging) apparatus.

FIG. 25 is a block diagram showing an example of the arrangement of a restoration function in a trained model when the medical imaging apparatus in FIG. 24 is an MRI apparatus. A restoration function 7 in FIG. 25 includes an FFT 71, a CNN 4, and an IFFT 72. The FFT 71 is applied to k-space data corresponding to an input signal to generate an input MR image. The CNN 4 is applied to the input MR image to generate an output MR image. The IFFT 72 is applied to the output MR image to generate k-space data. Providing the FFT 71 and the IFFT 72 for the restoration function allows the MRI apparatus to apply the CNN 4 to an MR image. Accordingly, the apparatus can use both CNN processing for an MR image and reliability data concerning k-space data, and hence can improve restoration accuracy.

Figure 26:
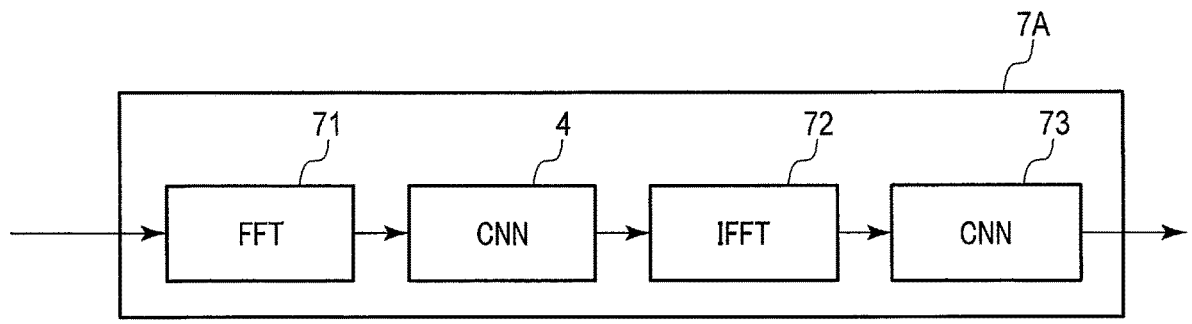
FIG. 26 is a block diagram showing another example of the arrangement of the restoration function in FIG. 25.

FIG. 26 is a block diagram showing another example of the arrangement of the restoration function in FIG. 25. A restoration function 7A in FIG. 26 includes an FFT 71, a CNN 4, an IFFT 72, and a CNN 73. Processing performed by the CNN 73 is almost the same as that performed by the CNN 4. The CNN 73 executes various types of computations for k-space data. In training filtering, the CNN 73 can be used for k-space data. Using the CNN 73 can improve the accuracy of subsequent k-space data. Note that the CNN may be executed before the FFT 71.

Processing circuitry 11 generates an output signal by applying a trained model to k-space data as an input signal and reliability data concerning the k-space data. In this case, the reliability data indicates the positions of phase-encode acquired and unacquired lines in k-space data which are acquired by using, for example, parallel imaging.

Figure 27:
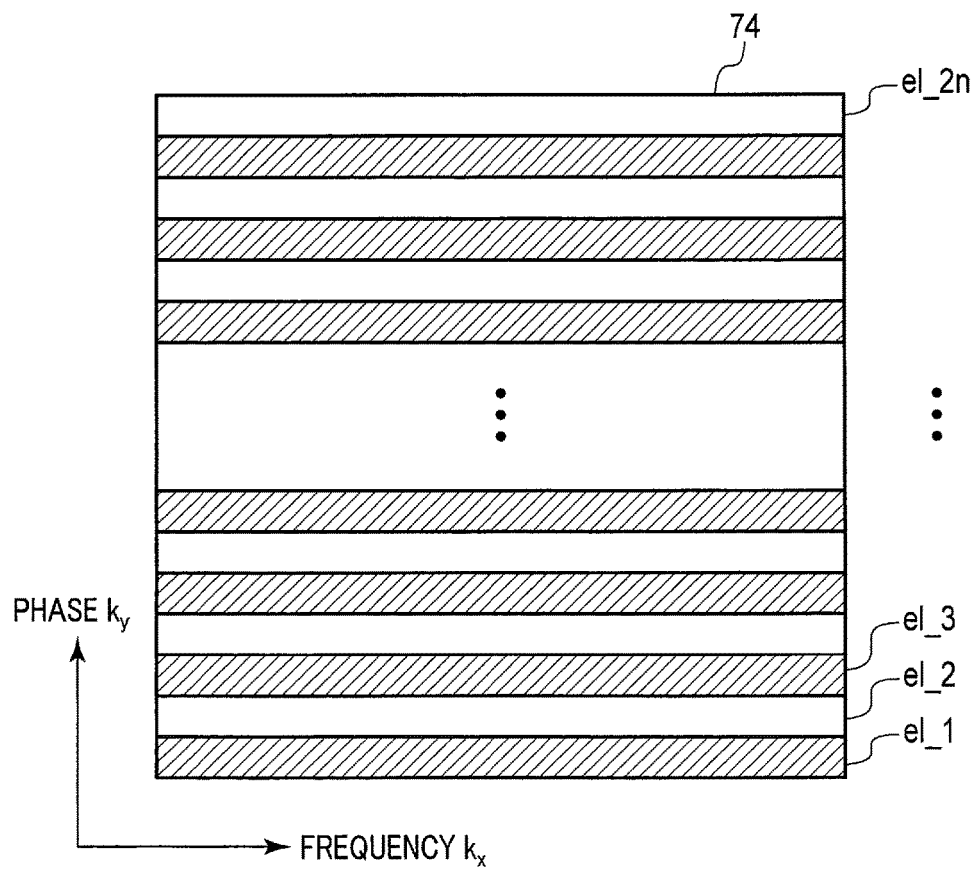
FIG. 27 is a view showing a specific example of k-space data including a lost portion when the medical imaging apparatus in FIG. 24 is an MRI apparatus.

FIG. 27 is a view showing a specific example of k-space data including a lost portion when the medical imaging apparatus in FIG. 24 is an MRI apparatus. Referring to FIG. 27, k-space data 74 includes acquired lines el_1, el_3, ..., el_2n-1 and unacquired lines el_2, el_4, ..., el_2n. Note that reliability data concerning the k-space data 74 indicates the positions of acquired lines or the positions of unacquired lines or both of them in the k-space data 74.

The following is a case, described with reference to FIG. 4, in which an output signal x is generated by applying a trained model 2A to the k-space data 74 corresponding to an input signal y and reliability data m concerning the k-space data 74.

A restoration function $R^{(o)}$ performs computation to generate restored k-space data from the k-space data 74. Assuming that the restoration function $R^{(o)}$ is provided with the above FFT and IFFT, an input MR image is generated by executing the FFT to the k-space data 74. In this case, when an input MR signal is generated, a k-space method is used for the k-space data 74, and unacquired lines of the k-space data 74 are estimated and loaded. A restored MR image is generated by, for example, applying the DNN to the input MR image, and restored k-space data is generated by executing IFFT for the restored MR image. Accordingly, restored k-space data is filled with unacquired lines unlike the k-space data 74.

A computing function $G^{(i)}$ performs computation to generate mask data by calculating the element-wise product of the restored k-space data and the reliability data m. The mask data is a data set obtained by, for example, extracting portions corresponding to unacquired lines of the k-space data 74 from the restored k-space data.

A restoration function $R^{(i)}$ performs computation to generate restored k-space data from the k-space data 74, the restored k-space data output from the preceding restoration function, and a mask signal.

The MRI apparatus performs data acquisition by using a plurality of reception coils, and respectively generates k-space data of a plurality of channels corresponding to the plurality of reception coils. The MR image reconstructed from the k-space data of each channel spatially weighted because the image is influenced by the spatial position and size of the reception coil. This weight is also called sensitivity. The above reconstructed MR image can be expressed in the form of original pixel values multiplied by the sensitivity.

When k-space data has a plurality of channels, the MRI apparatus may use computation including the sensitivity before and after FFT computation and IFFT computation. For example, upon acquiring k-space data alternately in the ky direction, the apparatus may insert computation to perform an unfolding process based on SENSE (Sensitivity encoding) method after FFT computation to convert k-space data into an MR image and multiply each pixel of each channel by the above sensitivity before IFFT computation. Accordingly, the restoration function $R^{(o)}$ and the restoration function $R^{(i)}$ can generate an MR image upon reducing the influences of the spatial position and size of the reception coil by performing computation in consideration of the sensitivity described above.

(Application Example in CT Apparatus)

When the medical imaging apparatus 6 is the gantry of a CT apparatus, the gantry irradiates an object with X-rays from an X-ray tube while rotating the X-ray tube and an X-ray detector around the object and detects X-rays transmitted through the object with the X-ray detector. The X-ray detector generates an electrical signal having a crest value corresponding to the dose of X-rays detected. Data acquisition circuitry applies signal processing such as A/D conversion to the electrical signal. The electrical signal having undergone the A/D conversion is called projection data or sinogram data. The projection data or sinogram data is transmitted as raw data to the signal restoration apparatus 1.

A case in which FBP (Filtered Back Projection) is used to generate a CT image from sinogram data, and Radon conversion is used to convert a CT image into sinogram data will be described next.

Figure 28:
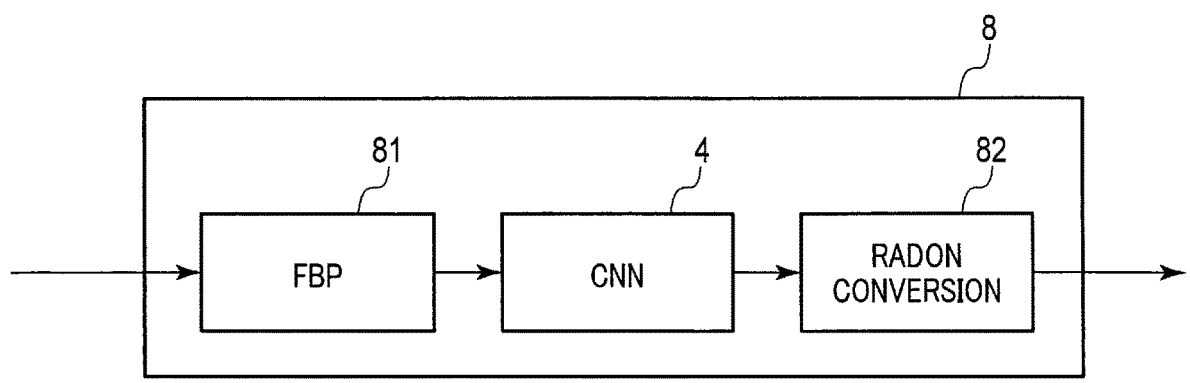
FIG. 28 is a block diagram showing an example of the arrangement of a restoration function in a trained model when the medical imaging apparatus in FIG. 24 is a CT (Computerized Tomography) apparatus.

FIG. 28 is a block diagram showing an example of the arrangement of a restoration function in a trained model when the medical imaging apparatus in FIG. 24 is a CT apparatus. A restoration function 8 in FIG. 28 includes an FBP 81, a CNN 4, and Radon conversion 82. The FBP 81 generates an input CT image from sinogram data corresponding to an input signal. The CNN 4 generates an output CT image from the input CT image. The Radon conversion 82 converts the output CT image into sinogram data. In this manner, letting the restoration function have the FBP 81 and the Radon conversion 82 makes it possible to apply the CNN 4 to a CT image.

The processing circuitry 11 generates an output signal by applying a trained model to sinogram data as an input signal and reliability data concerning the sinogram data. The reliability data in this case indicates, for example, the position of a metal artifact in sinogram data.

Figure 29:
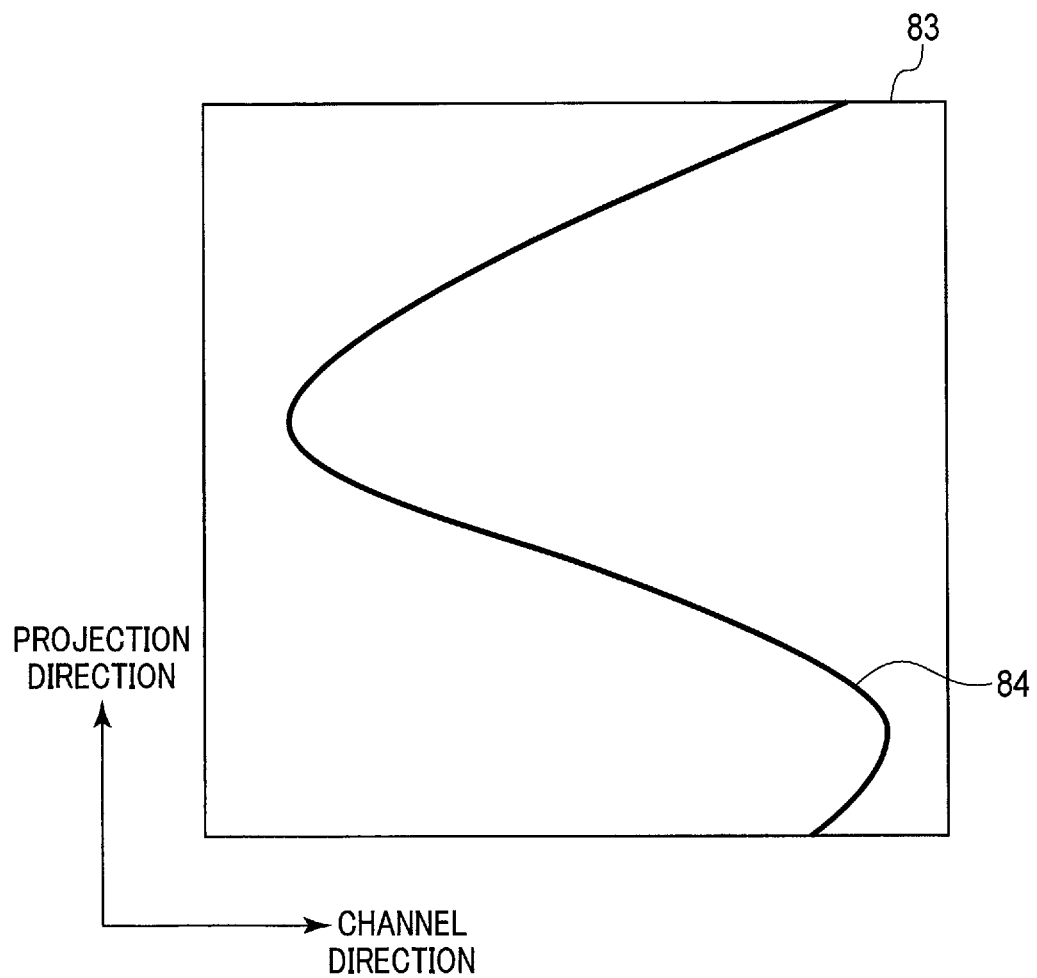
FIG. 29 is a view showing a specific example of sinogram data including a lost portion when the medical imaging apparatus in FIG. 24 is a CT apparatus.

FIG. 29 is a view showing a specific example of sinogram data including a lost portion when the medical imaging apparatus in FIG. 24 is a CT apparatus. Sinogram data 83 in FIG. 29 includes, for example, a lost portion 84 caused by a metal artifact. Note that reliability data concerning the sinogram data 83 indicates the position of a lost portion of the sinogram data 83.

The following is a case, described with reference to FIG. 4, in which the output signal x is generated by applying the trained model 2A to the sinogram data 83 corresponding to the input signal y and the reliability data m concerning the sinogram data 83.

The restoration function $R^{(o)}$ performs computation to generate restored sinogram data from the sinogram data 83. Assuming that the restoration function $R^{(o)}$ includes the above FBP and Radon conversion, an input CT image is generated by executing FBP for the sinogram data 83. For example, the DNN is applied to the input CT image to generate a restored CT image, and Radon conversion is executed for the restored CT image to generate restored sinogram data.

The computing function $G^{(i)}$ performs computation to generate a mask signal by calculating the element-wise product of the restored sinogram data and the reliability data m. A mask signal is obtained by, for example, extracting a portion of the restored sinogram data which corresponds to the lost portion 84 of the sinogram data 83 based on the reliability data m.

The restoration function $R^{(i)}$ performs computation to generate restored sinogram data from the sinogram data 83, the restored sinogram data output from the preceding restoration function, and a mask signal.

This embodiment can also be applied to a case in which a reduction in the reliability of acquired signal data or a data loss is caused by the movement of the bed during an examination by the CT apparatus as well as by a metal artifact.

(Application Example in PET Apparatus)

When the medical imaging apparatus 6 is the gantry of a PET apparatus, the gantry causes simultaneous measurement circuitry to simultaneously measure a pair of gamma rays of 512 keV generated accompanying the annihilation between positrons generated from radionuclides accumulated in an object and electrons existing around the radionuclides, thereby generating digital data having a digital value concerning the energy values and detection positions of the pair of gamma rays (LOR (Line Of Response)). This digital data is called coincidence data or sinogram data. The coincidence data or sinogram data is transmitted as raw data to the signal restoration apparatus 1.

According to the above arrangement, therefore, the medical image diagnostic apparatus according to the second embodiment includes the signal restoration apparatus according to the first embodiment. Accordingly, this medical image diagnostic apparatus can restore a medical image signal using more information that is not included in a medical image by using reliability data, and hence can improve the restoration accuracy of the medical image signal as compared with restoration by the DNN using only the medical image.

Third Embodiment

Figure 30:
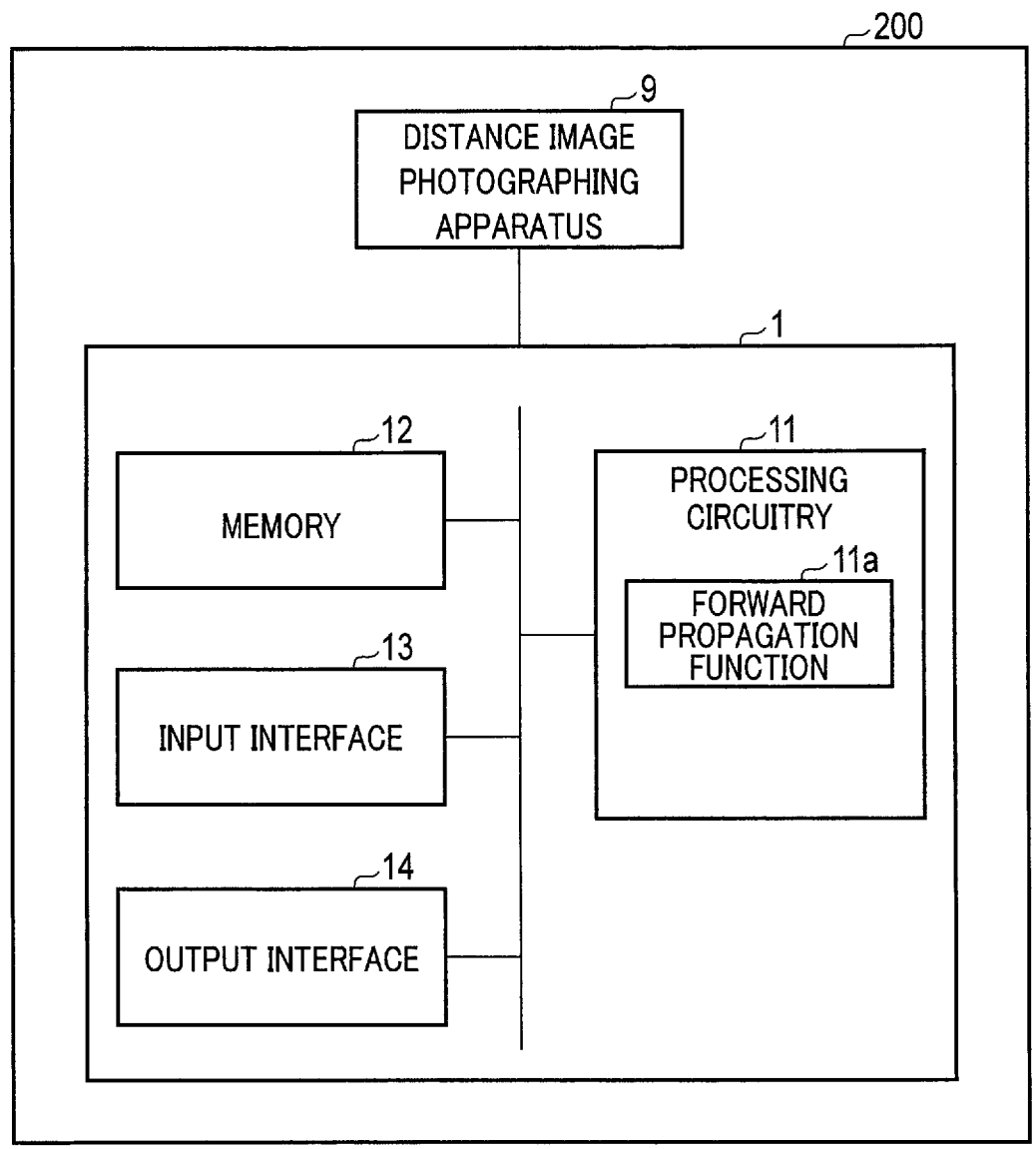
FIG. 30 is a block diagram showing an example of the arrangement of a distance image photographing system according to the third embodiment.

FIG. 30 is a block diagram showing an example of the arrangement of a distance image photographing system according to the third embodiment. A distance image photographing system 200 in FIG. 30 includes the signal restoration apparatus 1 according to the first embodiment and a distance image photographing apparatus 9. Note that the signal restoration apparatus 1 may be incorporated in the distance image photographing apparatus 9.

The distance image photographing apparatus 9 uses an optical remote sensing technique such as LIDAR (Light Detection And Ranging). LIDAR performs distance measurement by using, for example, laser light. More specifically, the distance image photographing apparatus 9 detects irradiation light emitted from the distance image photographing apparatus 9 and the reflected light when the irradiation light is reflected by a measurement target, and measures the distance from the distance image photographing apparatus 9 to a measurement target based on the times when the irradiation light and the reflected light are detected and the velocity of irradiation light. The distance image photographing apparatus 9 generates distance image data based on the distance to the measured measurement target. For example, distance image data is obtained by recording the data of the distance from the distance image photographing apparatus 9 to a measurement target for each pixel. The generated distance image data is transmitted as an input signal to the signal restoration apparatus 1. Note that the distance image data may be called depth information.

FIG. 31 is a view showing an example of distance image data and reliability data according to the third embodiment. Distance image data 91 in FIG. 31 includes an acquired portion 91a and an unacquired portion 91b. The acquired portion 91a is, for example, a range in which depth information up to the measurement target is acquired. The unacquired portion 91b is, for example, a range in which no depth information is acquired. More specifically, the unacquired portion 91b is generated in a case in which when irradiation light is reflected by an inclined surface, no reflected light can be obtained, or there is no reflecting object such as sky.

Processing circuitry 11 generates reliability data 92 by applying a reliability estimation function to the distance image data 91. The reliability estimation function may use, for example, a DNN or CNN. The reliability data 92 includes a high-reliability region 92a and a low-reliability region 92b. The high-reliability region 92a corresponds to the acquired portion 91a, and is represented by, for example, a numerical value between "0.9" and "1.0". The low-reliability region 92b corresponds to the unacquired portion 91b, and is represented by, for example, a numerical value between "0" and "0.1".

The following is a case, described with reference to FIG. 4, in which an output signal x is generated by applying a trained model 2A to the distance image data 91 corresponding to an input signal y and the reliability data 92 corresponding to reliability data m.

A restoration function $R^{(0)}$ performs computation to generate restored distance image data from the distance image data 91. A computing function $G^{(i)}$ performs computation to generate a mask signal by calculating the element-wise product of the restored distance image data and the reliability data 92. The mask signal is obtained by, for example, extracting a portion of the restored distance image data which corresponds to the unacquired portion 91b of the distance image data 91 based on the reliability data 92. The restoration function $R^{(i)}$ performs computation to generate restored distance image data from the distance image data 91, the restored distance image data output from the preceding restoration function, and the mask signal.

According to the above arrangement, therefore, a distance image photographing system according to the third embodiment includes the signal restoration apparatus according to the first embodiment. Accordingly, this distance image photographing system can restore a distance image signal using more information that is not included in a distance image by using reliability data, and hence can improve the restoration accuracy of the distance image signal as compared with restoration by the DNN using only the distance image.

According to at least one of the embodiments described above, it is possible to improve the restoration accuracy of signals.

The term "processor" used in the above description means, for example, a CPU, a GPU, or circuitry such as an ASIC (Application Specific Integrated Circuit), or a programmable logic device (for example, SPLD (Simple Programmable Logic Device), CPLD (Complex Programmable Logic Device), or FPGA (Field Programmable Logic Device)). The processor implements a function by reading out and executing a program saved in the storage circuitry. Note that a program may be directly incorporated in the circuitry of a processor instead of being stored in storage circuitry. In this case, the processor implements a function by reading out and executing a program incorporated in the circuitry of the processor. In addition, the function corresponding to the program may be implemented by a combination of logic circuits instead of executing the program. Note that each processor according to each embodiment described above may be formed as a single processor to implement its function by combining a plurality of independent circuits in addition of being formed as single circuitry for each processor. Furthermore, a plurality of constituent elements in FIGS. 1, 22, 24 or FIGS. 1, 22, and 30 may be integrated into one processor to implement the functions.

The instructions indicated in the processing procedure described in the above embodiments can be executed based on programs as software. A general-purpose computing system can obtain the same effects as those obtained by the signal restoration apparatus, the medical image diagnostic apparatus, and the distance image photographing system according to the respective embodiments described above by storing the programs in advance and loading the programs. The instructions described in the above embodiments are recorded as computer-executable programs in a magnetic disk (a flexible disk, hard disk, or the like), an optical disk (a CD-ROM, CD-R, CD-RW, DVD-ROM, DVD±R, DVD±RW, or the like), a semiconductor memory, or a similar recording medium. The storage form of a storage medium is not specifically limited as long as a computer or built-in system can read the medium. The computer can implement the same operations as those of the signal restoration apparatus, the medical image diagnostic apparatus, and the distance image photographing system according to the respective embodiments described above by reading the programs from the recording medium and causing the CPU to execute the instructions described in the programs based on the programs. Obviously, when the computer is to obtain or read programs, the computer may obtain or read the programs via a network.

In addition, an OS (Operating System) operating on a computer on the basis of instructions from programs installed from a storage medium into the computer or a built-in system, MW (middleware) such as database management software or network software, or the like may execute part of the processes for implementing this embodiment.

The storage medium in the present invention includes not only a medium independent of the computer or the built-in system but also a storage medium in which a program sent through a LAN (Local Area Network), Internet, or the like is downloaded and stored or temporarily stored.

In addition, the number of storage media is not limited to one. When the processing in the above embodiments is to be executed by using a plurality of media, the media are included in the storage media according to the embodiments, and the arrangement of each medium can be any arrangement.

Note that the computer or the built-in system according to each embodiment is designed to execute the respective processes in the embodiment based on the programs stored in the storage medium, and may take any arrangement, for example, an apparatus including a single device such as a personal computer or microcomputer or a system having a plurality of devices connected to each other through a network.

Furthermore, the computer according to each embodiment is not limited to a personal computer, and is a generic name for devices and apparatuses capable of implementing the functions of the embodiment based on programs, including arithmetic processing devices and microcomputers included in information processing devices.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
processing circuitry configured to:
generate initial restored signal data by applying a first restoration function to input signal data corresponding to medical signal data concerning an object;
generate first element-wise product signal data by calculating an element-wise product of the initial restored signal data and reliability data representing a degree of degradation included in the input signal data; and
generate restored signal data by applying a second restoration function to at least one of the input signal data and the initial restored signal data and the first element-wise product signal data.

2. The medical image diagnostic apparatus according to claim 1, further comprising a medical imaging apparatus configured to generate the medical signal data by performing medical imaging with respect to the object.

3. The medical image diagnostic apparatus according to claim 1, wherein the processing circuitry is further configured to generate second element-wise product signal data by calculating an element-wise product of the input signal data and the reliability data, and
when the second element-wise product signal data is generated,
the processing circuitry is further configured to generate the restored signal data by applying the second restoration function to at least one of the input signal data and the initial restored signal data, the first element-wise product signal data, and the second element-wise product signal data.

4. The medical image diagnostic apparatus according to claim 1, wherein the second restoration function is formed by using at least one of a deep neural network, a convolution neural network, and a recurrent neural network.

5. The medical image diagnostic apparatus according to claim 2, wherein the medical signal data is k-space data, the input signal data corresponding to the k-space data, and
the processing circuitry is further configured to generate a magnetic resonance image by applying image restoration processing to the restored signal data.

6. A medical image diagnostic apparatus comprising:
processing circuitry configured to:
generate initial restored signal data by applying a first restoration function to input signal data corresponding to medical signal data concerning an object;

generate element-wise product signal data by calculating an element-wise product of the input signal data and reliability data representing a degree of degradation included in the input signal data; and generate restored signal data by applying a second restoration function to the initial restored signal data and the element-wise product signal data.

7. The medical image diagnostic apparatus according to claim 6, further comprising a medical imaging apparatus configured to generate the medical signal data by performing medical imaging with respect to the object.

8. The medical image diagnostic apparatus according to claim 6, wherein the processing circuitry is further configured to generate the restored signal data by applying the second restoration function to the input signal data, the initial restored signal data, and the element-wise product signal data.

9. The medical image diagnostic apparatus according to claim 6, wherein the second restoration function is formed by using at least one of a deep neural network, a convolution neural network, and a recurrent neural network.

10. The medical image diagnostic apparatus according to claim 7, wherein the medical signal data is k-space data, the input signal data corresponding to the k-space data, and the processing circuitry is further configured to generate a magnetic resonance image by applying image restoration processing to the restored signal data.

11. A medical signal restoration method comprising:

generating initial restored signal data by applying a first restoration function to input signal data corresponding to medical signal data concerning an object;

generating first element-wise product signal data by calculating an element-wise product of the initial restored signal data and reliability data representing a degree of degradation included in the input signal data; and generating restored signal data by applying a second restoration function to at least one of the input signal data and the initial restored signal data and the first element-wise product signal data.

12. The medical signal restoration method according to claim 11, further comprising generating the medical signal data by performing medical imaging with respect to the object.

13. The medical signal restoration method according to claim 11, wherein the second restoration function is formed by using at least one of a deep neural network, a convolution neural network, and a recurrent neural network.

14. A model training method comprising:

generating estimated restored signal data corresponding to the restored signal data by applying the medical signal restoration method defined in claim 11 to input signal data corresponding to medical signal data and reliability data representing a degree of degradation included in the input signal data;

updating a parameter of a second restoration function applied to generate restored signal data so as to approximate the estimated restored signal data to correct output signal data corresponding to the input signal data; and outputting a trained model concerning the updated second restoration function.

15. The model training method according to claim 14, wherein the second restoration function is formed by using at least one of a deep neural network, a convolution neural network, and a recurrent neural network.

* * * * *